US008563931B2

(12) United States Patent
Abbas et al.

(10) Patent No.: US 8,563,931 B2
(45) Date of Patent: Oct. 22, 2013

(54) SYSTEM FOR PROVIDING A CALIBRATION FOR A TESTING DEVICE USED TO EVALUATE ETHANOL PRODUCTION YIELD, AND ASSOCIATED METHOD

(75) Inventors: Jason Abbas, Perry, IA (US); George Aux, Durham, NC (US); Joe Byrum, West Des Moines, IA (US); My Nguyen, Ankeny, IA (US); Kirk Noel, Granger, IA (US); Mark P Seymour, Bracknell (GB)

(73) Assignee: Syngenta Participations AG, Basel (CH)

( * ) Notice: Subject to any disclaimer, the term of this patent is extended or adjusted under 35 U.S.C. 154(b) by 702 days.

(21) Appl. No.: 12/626,319

(22) Filed: Nov. 25, 2009

(65) Prior Publication Data
US 2010/0148048 A1  Jun. 17, 2010

Related U.S. Application Data

(60) Provisional application No. 61/200,189, filed on Nov. 25, 2008, provisional application No. 61/200,225, filed on Nov. 25, 2008.

(51) Int. Cl.
*G01J 5/00* (2006.01)
*G12B 13/00* (2006.01)

(52) U.S. Cl.
USPC ............................ 250/338.1; 250/252.1

(58) Field of Classification Search
USPC ............ 250/252.1, 338.1; 426/531; 435/161, 435/162
See application file for complete search history.

(56) References Cited

U.S. PATENT DOCUMENTS

| | | | |
|---|---|---|---|
| 5,751,421 A | * | 5/1998 | Wright et al. ............... 356/328 |
| 5,991,025 A | | 11/1999 | Wright et al. |
| 6,483,583 B1 | | 11/2002 | Wright et al. |
| 6,885,003 B1 | | 4/2005 | Dubernet |
| 7,274,456 B2 | | 9/2007 | Wright |
| 2003/0135885 A1 | | 7/2003 | Lanahan et al. |
| 2010/0151440 A1 | | 6/2010 | Abbas et al. |

OTHER PUBLICATIONS

Davis. 2001. Corn Milling, Processing and Generation of Co-products, Minnesota Nutrition Conference Minnesota Corn Growers Association Technical Symposium. Sep. 11, 2001, p. 1-7.
Smith. 2008. Brewing an Irish Stout Beer Recipe. Beer Smith Home Brewing Blog, Mar. 14, 2008, pp. 1-3.
Singh et al. 1996. Wet Milling of Corn—A Review of Laboratory-Scale and Pilot Plant-Scale Procedures. Cereal Chemistry, vol. 73, No. 6, pp. 659-667.
Comberbach, et al. 1983. Automatic on-line fermentation headspace gas analysis using a computer-controlled gas chromatograph. Biotechnology and Bioengineering, vol. 25, Issue 11, pp. 2503-2518.

* cited by examiner

*Primary Examiner* — Mark R Gaworecki
(74) *Attorney, Agent, or Firm* — Dana Rewoldt; R. Kody Jones

(57) ABSTRACT

A system with a first analytical testing device configured collect a first and second signal associated with a characteristic parameter of a sample material, wherein the characteristic parameter is capable of enabling evaluation of ethanol production yield for plant material corresponding to the sample material. A drying unit is configured to drive the sample material to a substantially standard moisture level. A fermentation unit is configured to ferment the sample material. A second analytical testing device is configured to collect a reference measurement associated with the characteristic parameter. The reference measurement is capable of being correlated to the first and second signals for building a calibration model used to evaluate ethanol production yield of plant material corresponding in composition to the sample material. Associated methods are also provided.

32 Claims, 14 Drawing Sheets

SYSTEM FOR PROVIDING A CALIBRATION FOR A TESTING DEVICE USED TO EVALUATE ETHANOL PRODUCTION YIELD, AND ASSOCIATED METHOD

REFERENCE TO RELATED APPLICATION

This application claims the benefit of priority two U.S. Provisional Application Ser. No. 61/200,225 and 61/200,189 filed on Nov. 25, 2008.

BACKGROUND

1. Field of the Invention

This invention relates to calibrating for analytical testing devices, and more particularly to calibrating for an analytical testing device used for evaluating ethanol production yield of an ethanol-producing biological material in a high throughput manner.

2. Description of Related Art

Ethanol fermentation is a biological process in which organic material is converted by microorganisms to simpler compounds, such as sugars. These fermentable compounds are then fermented by microorganisms to produce ethanol and $CO_2$. Ethanol has widespread application, including, as an industrial chemical, gasoline additive or straight liquid fuel. As a fuel or fuel additive, ethanol dramatically reduces air emissions while improving engine performance. As a renewable fuel, ethanol reduces national dependence on finite and largely foreign fossil fuel sources, while decreasing the net accumulation of carbon dioxide in the atmosphere.

As such, ethanol-producing plant materials are valuable crops with many industrial uses due to their unique chemical composition. The amount of ethanol produced from plant material, such as, for example, corn feedstock, can depend on the amount and availability of starch in the plant material, milling conditions, the type of yeast used, the fermentation conditions, and the like. Generally, plant varieties for use in ethanol production are selected based on the fermentability of the variety. Accordingly, seed breeders are continually trying to develop varieties of seeds to maximize ethanol yield. As such, ethanol producers (i.e., purchasers of the plant material) prefer quality control testing for determining the expected ethanol yield for a batch of plant material prior to processing thereof. Previously, correlations between starch and protein levels have been made for evaluating ethanol yield in plant material prior to production processing steps. Such determinations have traditionally been carried out in laboratories, which implement techniques that typically are laborious and time consuming, such as wet chemistry techniques (e.g., high performance liquid chromatography). In this regard, such analyses further have been typically carried out in large vessels and have involved recalculating the ethanol contents of a sample material based on an inconsistent moisture level, both of which may impede throughput for analyzing the ethanol yield of the sample material. One conventional evaluation technique grinds agricultural seed into a homogenous powder, wherein any of a variety of laboratory techniques can then be utilized to derive information about the chemical make-up of the powder. In this regard, information can be collected and used through destruction of the seed. As such, significant time and resources are required to grind and handle individual seed and its powdered form.

Thus, it would be desirable to provide an objective and rapid qualitative evaluation of plant seed material intended for ethanol production in a non-destructive manner. Such an evaluation would make it possible to determine objectively the ethanol yield of the plant seed material according to its quality/composition. In this regard, it would be advantageous to carry out this objective analysis quickly at ethanol production sites (and not only in a laboratory). Furthermore, it would be advantageous to calibrate for a device implementing such a rapid qualitative evaluation of plant seed material, wherein a calibration system and/or method facilitates high throughput of a sample material to build a calibration model associated with the plant material to be used in large-scale ethanol production.

SUMMARY OF THE INVENTION

The above and other needs are met by the present invention which, according to one aspect, provides a system used to calibrate for a near infrared analytical testing device configured to screen for ethanol production yield of an ethanol-producing plant material. The system comprises a first analytical testing device configured to interact with a sample material and collect a first signal associated with a characteristic parameter of the sample material. The characteristic parameter is capable of enabling evaluation of ethanol production yield for plant material corresponding to the sample material. A drying unit is in communication with the first analytical testing device, and is configured to drive the sample material to a substantially standard moisture level, so as to form a dried sample material. The first analytical testing device is further configured to interact with the dried sample material and collect a second signal associated with the characteristic parameter. A fermentation unit is in communication with at least one of the drying unit and the first analytical device, and is configured to ferment the dried sample material, so as to form a fermented sample material. A second analytical testing device is in communication with the fermentation unit, and is configured to interact with the fermented sample material and collect a reference measurement associated with the characteristic parameter. The reference measurement is capable of being correlated to at least one of the first and second signals for building a calibration model used to evaluate ethanol production yield of plant material corresponding substantially in composition to the sample material.

Another aspect provides a method of calibrating for a near infrared analytical testing device configured to screen for ethanol production yield of an ethanol-producing plant material. Such a method comprises collecting a first signal associated with a sample material with a first analytical testing device. The first signal is associated with a characteristic parameter of the sample material, wherein the characteristic parameter is capable of enabling evaluation of ethanol production yield for plant material corresponding to the sample material. The method further comprises drying the sample material to a substantially standard moisture level, and collecting a second signal associated with a sample material with the first analytical testing device, wherein the second signal is associated with the characteristic parameter. The method further comprises fermenting the sample material and collecting a reference measurement associated with the sample material with a second analytical testing device, wherein the reference measurement is associated with the characteristic parameter of the sample material. The method further comprises correlating the reference measurement to the first signal to a calibration model used to evaluate ethanol production yield of plant material corresponding substantially in composition to the sample material.

Yet another aspect provides a method of calibrating for a near infrared analytical testing device configured to screen for ethanol production yield of an ethanol-producing material. Such a method comprises grinding an agricultural material to form a sample material, and collecting a first near infrared signal associated with the sample material with a near infrared testing device, wherein the first near infrared signal is associated with a characteristic parameter of the sample material, and further wherein the characteristic parameter is capable of enabling evaluation of ethanol production yield for plant material corresponding to the sample material. The method further comprises drying the sample material to a substantially standard moisture level. A second near infrared signal is collected with the near infrared testing device, wherein the second near infrared signal is associated with the characteristic parameter. The sample material is fermented. A reference measurement associated with the sample material is collected with a gas chromatography testing device, wherein the reference measurement is associated with the characteristic parameter. The reference measurement is correlated to at least one of the first and second near infrared signals to build a calibration model used to evaluate ethanol production yield of plant material corresponding substantially in composition to the sample material.

The high throughput processing of sample material disclosed herein is suitable for building a calibration model for use with a device capable of facilitating rapid evaluation of a characteristic parameter used in evaluating ethanol yield of an ethanol-producing material.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a schematic representation of a system used to calibrate for a near infrared analytical testing device configured to screen for ethanol production yield of an ethanol-producing material, according to one embodiment of the present invention;

FIG. 2 is a flow chart of a method according to one embodiment of the present invention including the steps of collecting a first signal associated with a sample material, drying the sample material to a substantially standard moisture level, collecting a second signal associated with a sample material, fermenting the sample material, collecting a reference measurement associated with the sample material, and correlating the reference measurement to at least one of the first and second signals;

FIG. 3 is a schematic representation of a system used to calibrate for a near infrared analytical testing device configured to screen for ethanol production yield of an ethanol-producing material, wherein the system includes a third analytical testing device, according to one embodiment of the present invention;

FIG. 4 is representation of a system used to calibrate for a near infrared analytical testing device configured to screen for ethanol production yield of an ethanol-producing material, wherein the system includes a preparation unit (which can be a grinding unit) unit, according to one embodiment of the present invention; and FIG. 5 is a flow chart of a method according to one embodiment of the present invention including the steps of preparing an agricultural material to form a sample material, collecting a first near infrared signal associated with the sample material, drying the sample material to a substantially standard moisture level, collecting a second near infrared signal associated with a sample material, fermenting the sample material, collecting a reference measurement associated with the sample material, and correlating the reference measurement to at least one of the first and second near infrared signals.

FIG. 8 A is the calibration curve for the 1% front dual at 24 hours.

FIG. 8 B is the calibration curve for the 1% back dual at 24 hours.

FIG. 8 C is the calibration curve for the 1% front dual at 48 hours.

FIG. 8 D is the calibration curve for the 1% back dual at 48 hours.

FIG. 8 E is the calibration curve for the 1% front dual at 72 hours.

FIG. 8 F is the calibration curve for the 1% back dual at 72 hours.

FIG. 8 G is the calibration curve for the 2.5% front dual at 24 hours.

FIG. 8 H is the calibration curve for the 2.5% back dual at 24 hours.

Figure 9:
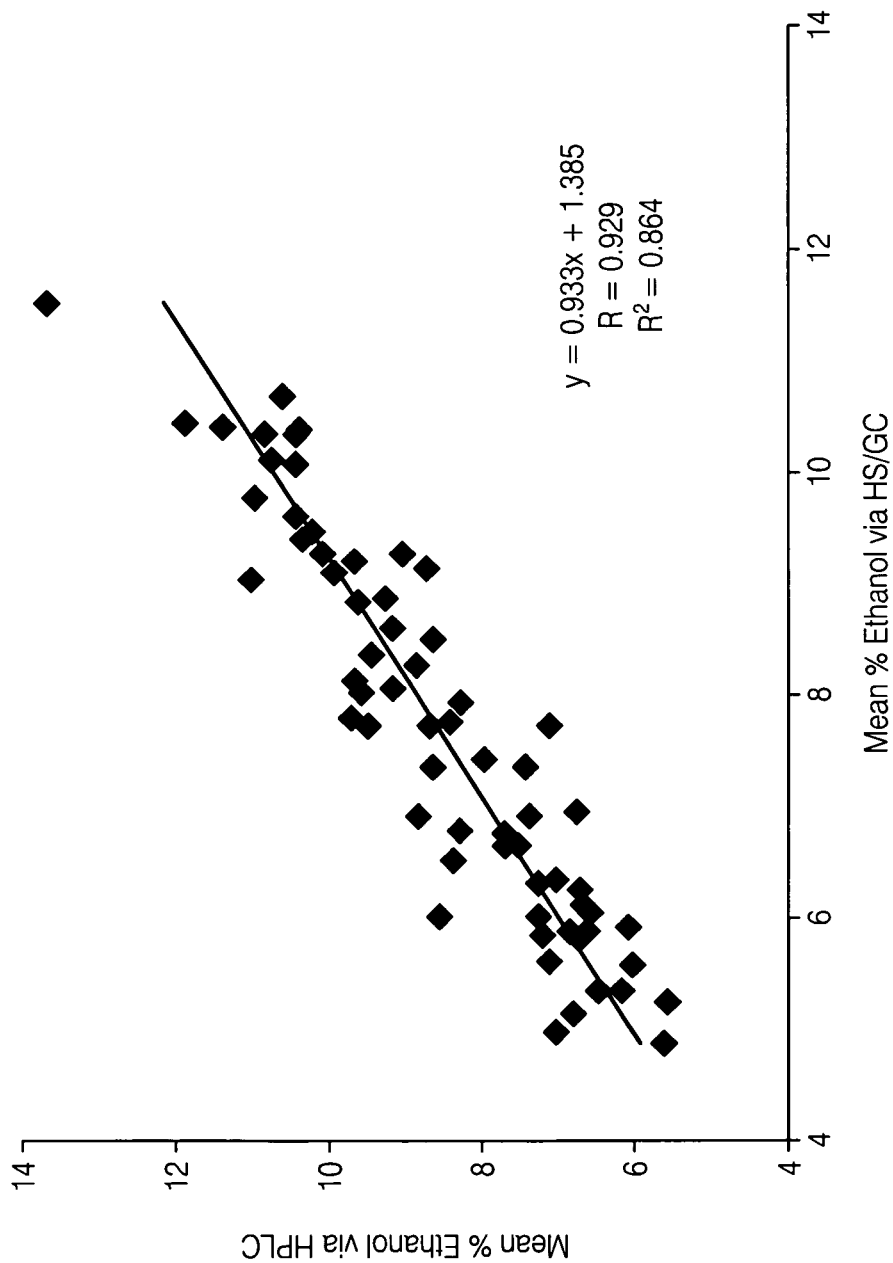

FIG. 9 illustrates the plotted data and fitted regression line of the Plot of Mean % Ethanol via HS/GC vs. Mean % Ethanol via HPLC from Experiment 5.

DETAILED DESCRIPTION OF THE INVENTION

The present disclosure now will be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention are directed to systems and methods used to calibrate for a near infrared analytical testing device configured to screen for ethanol production yield of an ethanol-producing plant material. That is, embodiments of the present invention are provided to increase throughput of sample analysis of sample materials used in compiling data and building a calibration model for a device configured to rapidly evaluate ethanol-producing materials for ethanol yield. For example, such a calibration model may be adapted for use with a portable near infrared (NIR) spectrometer device capable of screening raw agricultural material (e.g., seed, flour, raw starch) for desired ethanol yields.

In one embodiment of the invention, the methods of the present invention generally comprise providing a sample comprised of biological material capable of producing ethanol. The sample may be optically analyzed to provide a spectra associated with characteristics for the sample. Such spectra can then be correlated to fermentation measurements in order to determine the ethanol yield of the sampled biological material.

Near infrared spectroscopy is well-known for analyzing substances for chemical makeup. Advantageously, NIR analysis is non-destructive, cost-efficient, and time-efficient, while allowing for analysis by non-highly-skilled workers. It directs electromagnetic energy in the near infrared (NIR) spectrum at a specimen and detects the transmittance and/or reflectance of that energy. Evaluation of absorption of the energy reveals chemical makeup of the portion of the specimen interrogated. Such use of NIR to evaluate agricultural grain is also well known, as disclosed in U.S. Pat. Nos. 5,751,421; 5,991,025; and 6,483,583 to Wright et al.; and U.S. Pat. No. 7,274,456, each of which is incorporated by reference herein. However, the need for providing a calibration for various biological materials in a quick and efficient manner is not addressed in these patents. In this regard, NIR analysis is typically carried out with calibration models provided by the NIR spectrometer manufacturer or some third party.

Embodiments of the present invention are thus provided to increase throughput of sample analysis for biological materials used in calibrating for an analytical testing device, such as, for example, an NIR spectrometer device, used to evaluate ethanol yield of the biological material for screening purposes. In this regard, embodiments of the present invention generally provide increased efficiency in preparing a calibration model for use in such an analytical testing device used to evaluate ethanol yield of a biological material. The calibration process provides performing ethanol production in a small-scale manner to allow screening of multiple samples simultaneously. Such a platform provides a significant advantage over full-scale conventional ethanol production processes in that multiple reactions can be performed in a significantly reduced amount of time. For the purposes of the present invention, a "conventional ethanol production process" comprises liquefaction of at least about 25 grams of processed plant material (e.g., ground samples) in the presence of one or more starch-degrading enzymes, fermentation of the resulting mash in a fermentation vessel for at least about 72 hours, and measurement of ethanol production using high-performance liquid chromatography. In various embodiments, the number of ethanol conversion reactions that can be performed using the systems and methods disclosed herein is at least about 5 times, or at least about 10 times, the number of reactions that can be performed in the same amount of time and space as conventional ethanol conversion processes.

Embodiments of the present invention may be applied to plant material derived from any of a variety of plants, including, but not limited to maize, wheat, rice, barley, soybean, cotton, sorghum (milo), oats, beans in general, rape/canola, alfalfa, flax, sunflower, safflower, millet, rye, sugarcane, sugar beet, cocoa, tea, Brassica, cotton, coffee, sweet potato, flax, peanut, clover; grasses and trees; vegetables such as lettuce, tomato, cucurbits, cassava, potato, carrot, radish, pea, lentils, cabbage, cauliflower, broccoli, Brussels sprouts, peppers, and pineapple; fruits such as citrus, grapes, pineapple, apples, pears, peaches, apricots, walnuts, avocado, plantain, banana, and coconut; and flowers such as orchids, carnations and roses.

As used herein, the term "plant part," "plant material," or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The plant material can also be obtained as a previously treated plant product such as soy cake generated during the processing of soybeans. The plant material can be a mixture of such materials and by-products of such materials, e.g., corn fiber, corn cobs, stover, or other cellulose- and hemicellulose-containing materials, such as wood or plant residues. In various embodiments, the plant materials include corn, either standard corn, mutant corn, transgenic corn or waxy corn.

Furthermore, starch-containing plant material useful in the system and method embodiments of the present invention can be derived from a transgenic or a nontransgenic plant. As used herein the term "transgenic" refers to plants that include a heterologous polynucleotide. A heterologous polynucleotide can be a polynucleotide isolated from one species and then transferred back into the same species or a different species. The term "transgenic plant" can refer either to the initially transformed plant or to the progeny of the initially transformed plant. Techniques for transforming plants, plant cells or plant tissues can include, but are not limited to, transformation with DNA employing A. tumefaciens or A. rhizo genes as the transforming agent, electroporation, DNA injection, microprojectile bombardment, and particle acceleration. See, for example, EP 295959 and EP 138341.

The starch-containing plant material used herein may be an admixture of different types of plant materials. The term "admix" or "admixture" refers to a combination of elements. For example, an admix of plant material can refer to mixing two or more plant materials together to form a mixture. It is possible to further define the admixture by indicating the percentage of one or more of the elements. The plant material can be comprised of nontransgenic material or both transgenic and non-transgenic plant or just transgenic material. Transgenic plant material can contain a heterologous transgene encoding an enzyme, an insect control gene, an herbicide tolerance gene, a phytase, a nematode control gene or any other transgenic gene. The transgenic material may express more than one transgene.

The starch-containing plant material can be from a source (e.g., a plant strain) that is known to produce a relatively high level of fermentable sugars upon liquefaction and/or saccharification, or that has been bred or engineered to have some other advantageous property (e.g., pest or drought resistance). In some embodiments, more than two starch-containing plant materials can be used. Any combination of transgenic and nontransgenic plants can be used.

The ratio of non-starch-degrading enzyme-expressing plant material and starch-degrading enzyme-expressing plant material can be modeled in any suitable ratio so that the amount of starch-degrading enzyme in the mash is sufficient to digest the starch to produce glucose in a suitable amount of time or to produce a mixture that contains a desired level of glucose. Similarly, the ratio of the different starch-degrading enzyme-expressing plant materials can be modeled to facilitate a desired amount of saccharification in a desired amount of time.

Following long-standing patent law convention, the terms "a" and "an" mean "one or more" when used in this application, including the claims. Thus, "an enzyme" or "a plant material" can refer to a plurality (i.e., two or more) enzymes or plant materials. As used herein, the term "about" modifying any amount can refer to the variation in that amount encountered in real world conditions of producing sugars and ethanol, e.g., in the lab, pilot plant, or production facility. Unless otherwise indicated, all numbers expressing quantities of percentage, weight, temperature, flow rate, time, pH, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

Figure 1:
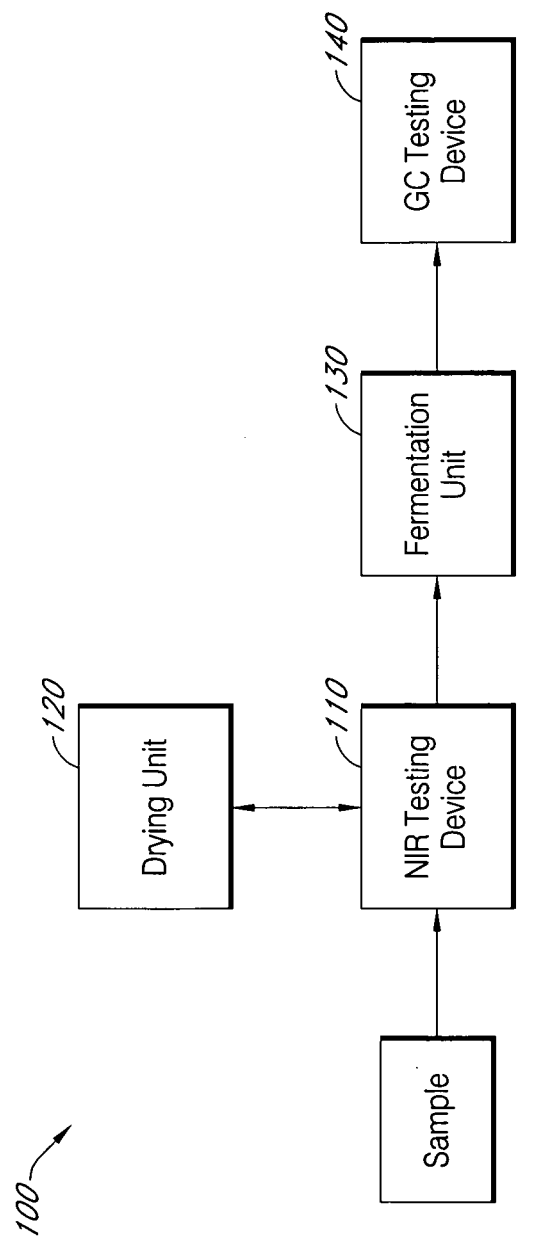
Figure 2:
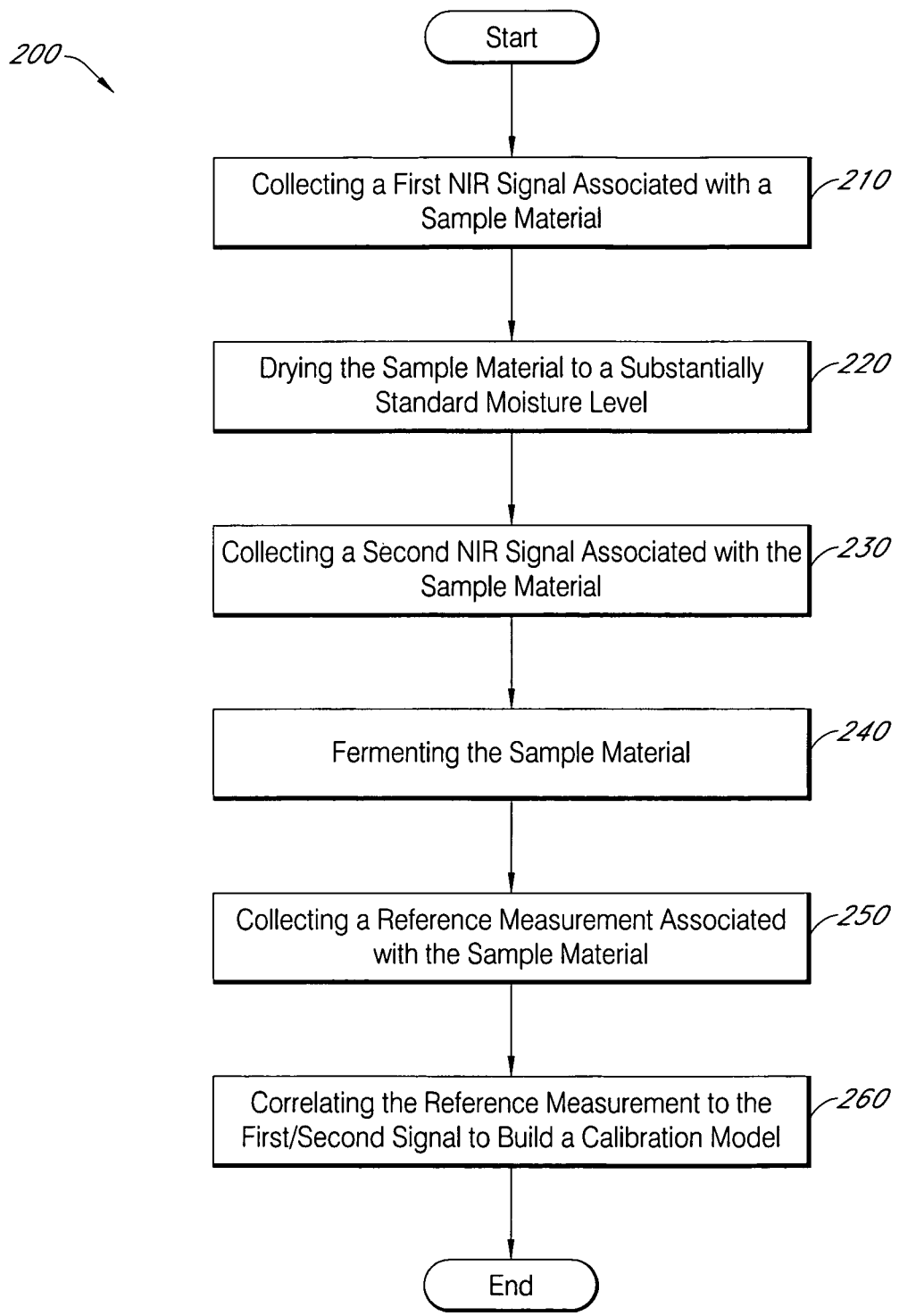
Figure 3:
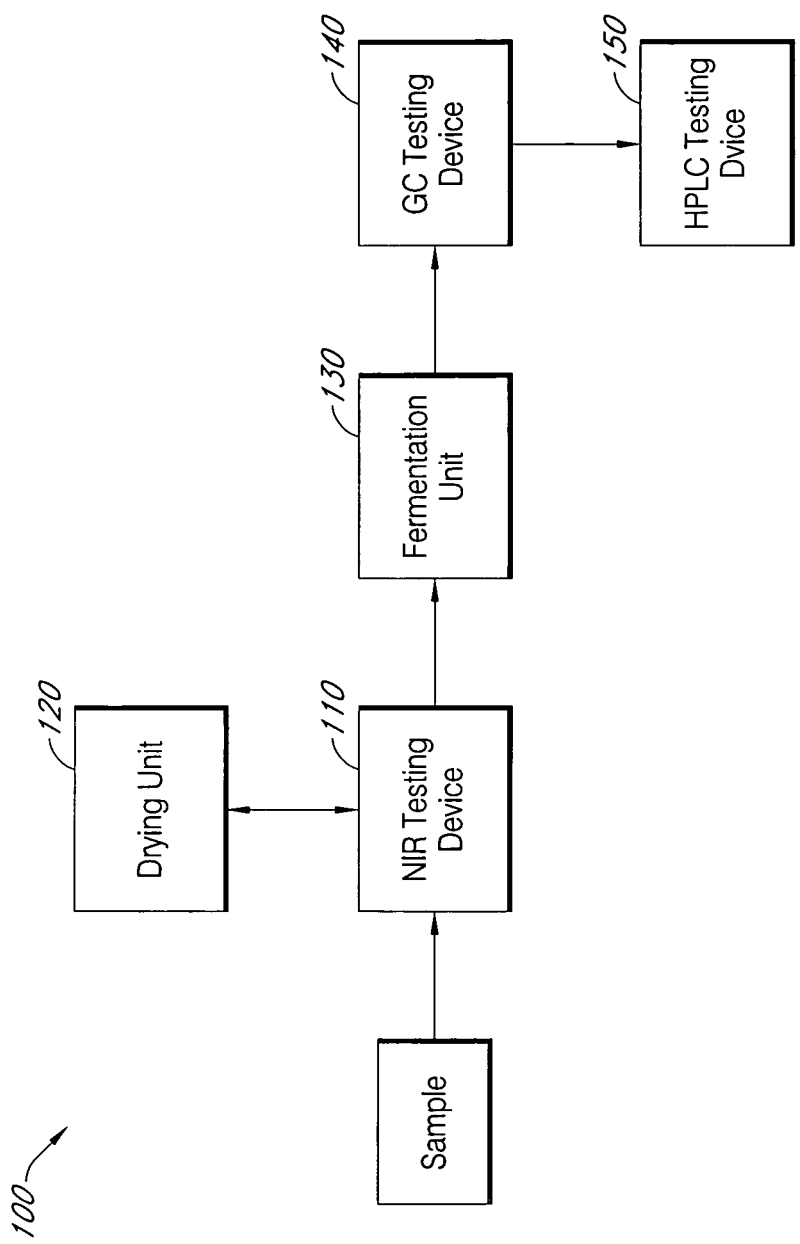
Figure 4:
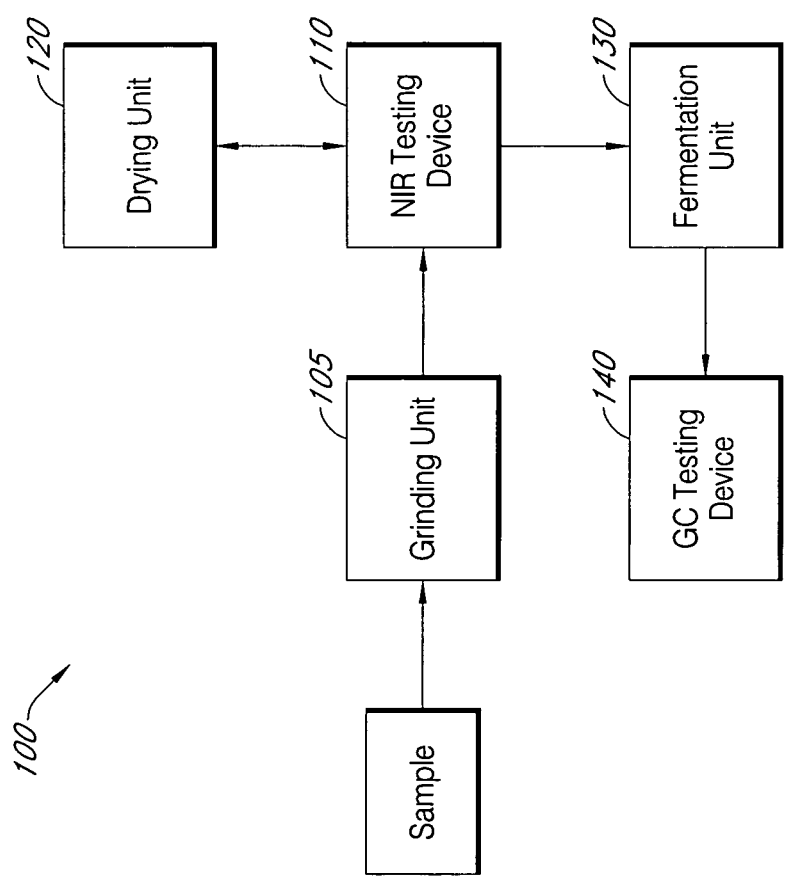
Figure 5:
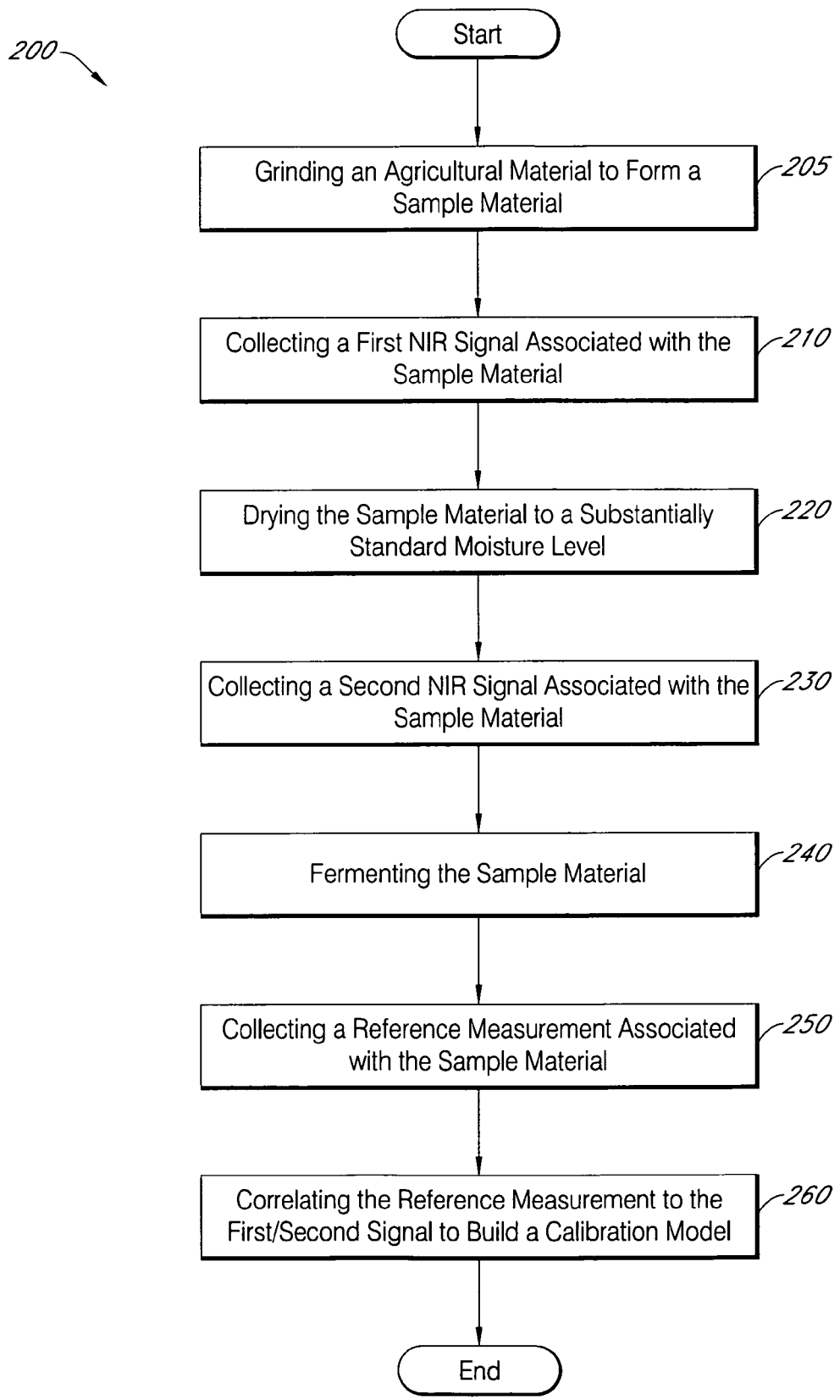
Figure 6:
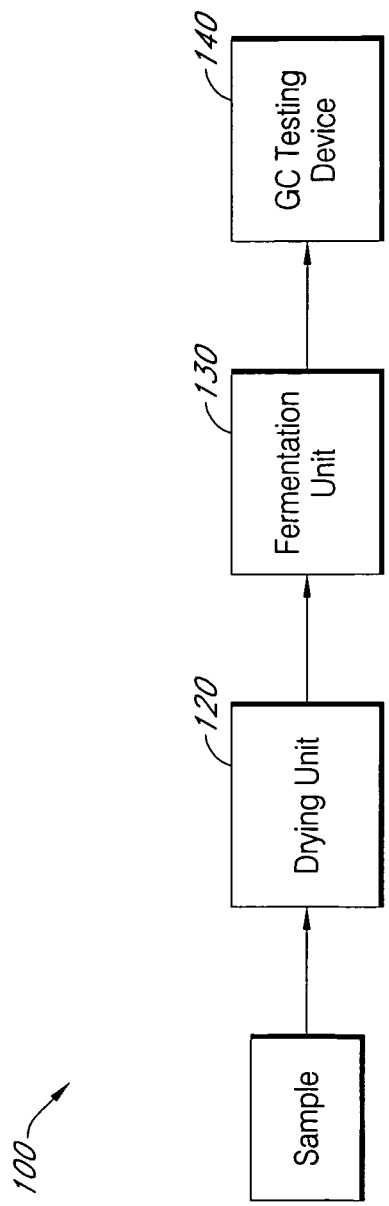
FIG. 6 is a schematic representation of a system used in a testing device configured to screen for ethanol production yield of an ethanol-producing material, according to one embodiment of the present invention.
Figure 7A:
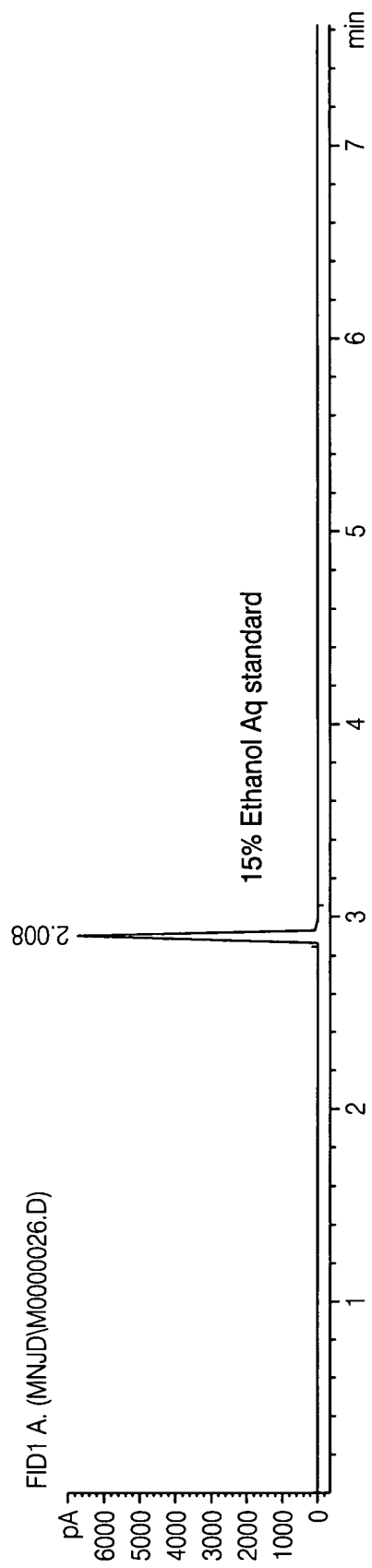
FIG. 7A is a sample chromatogram 15% Ethanol Standard, from the experiment 3.
Figure 7B:
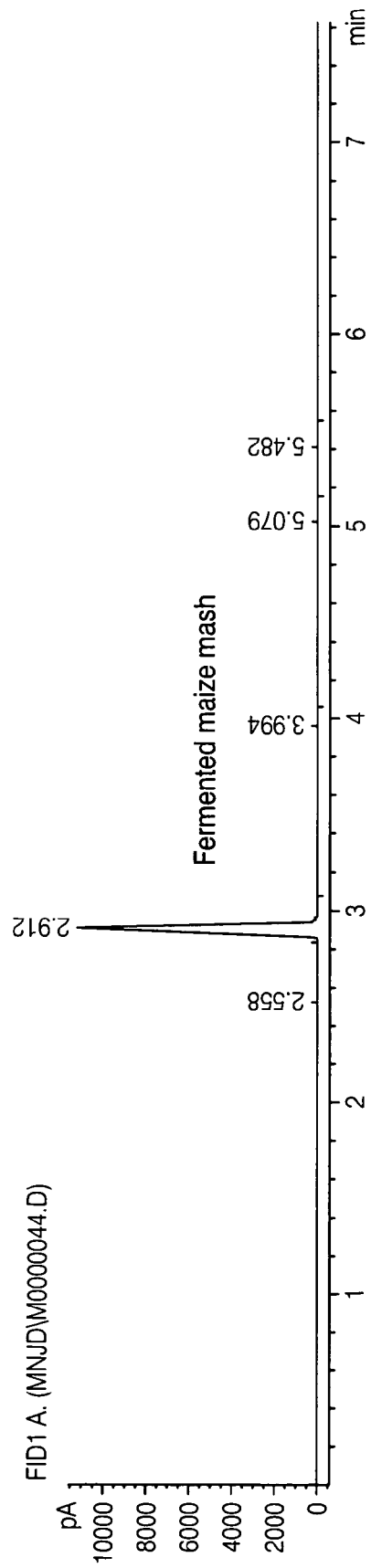
FIG. 7B is a sample chromatogram Fermented Maize, from the experiment 3.
Figure 7C:
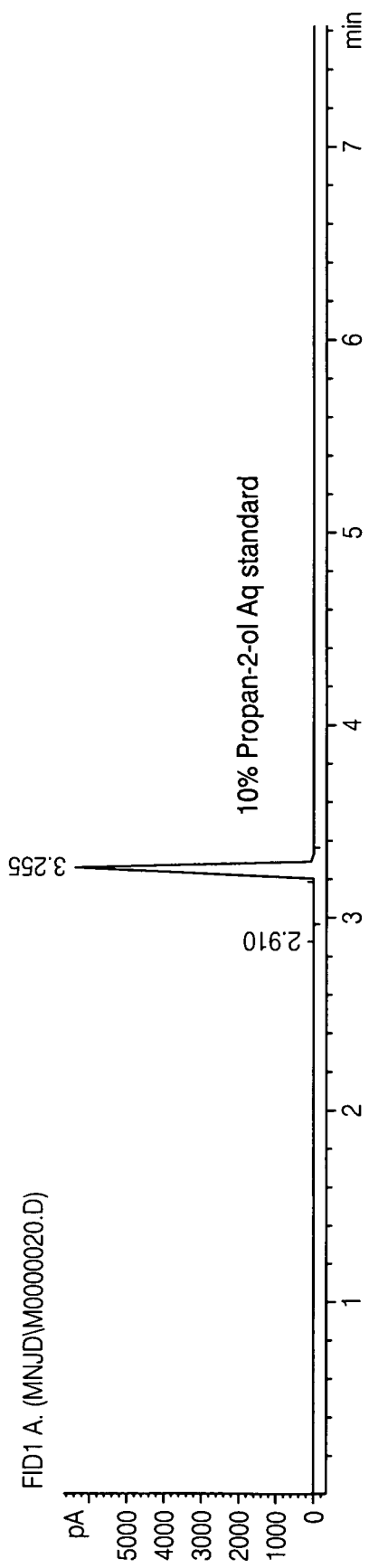
FIG. 7C is a sample chromatogram 10% Isopropanol Standard, from the experiment 3.
Figure 8A:
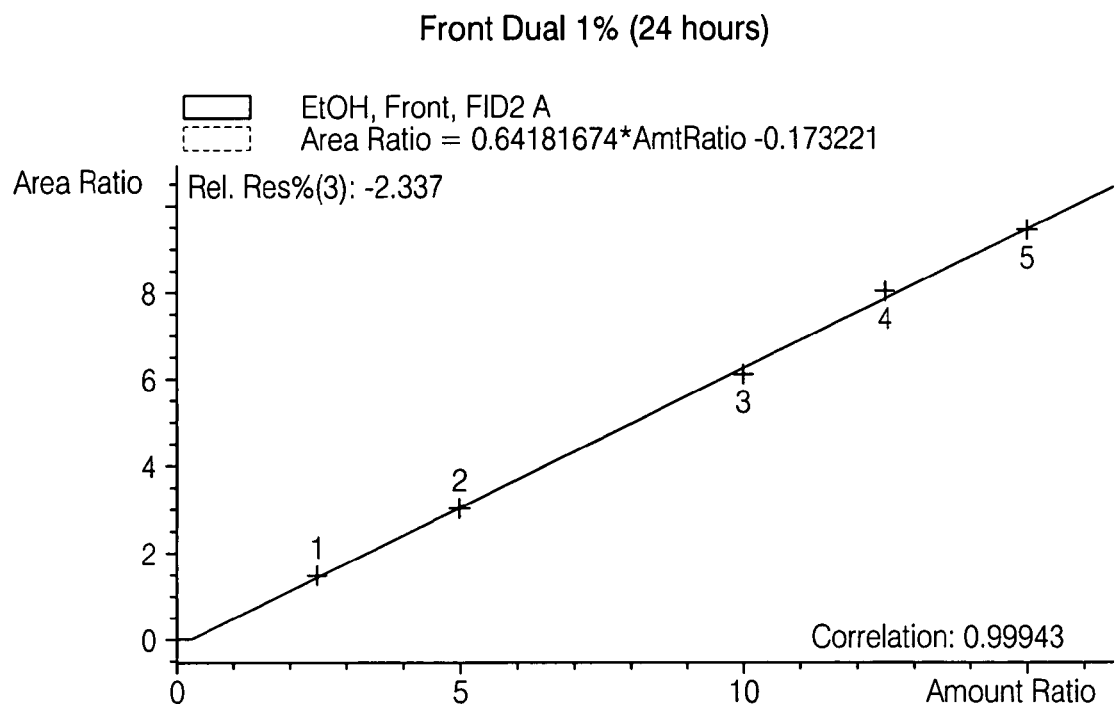
Figure 8B:
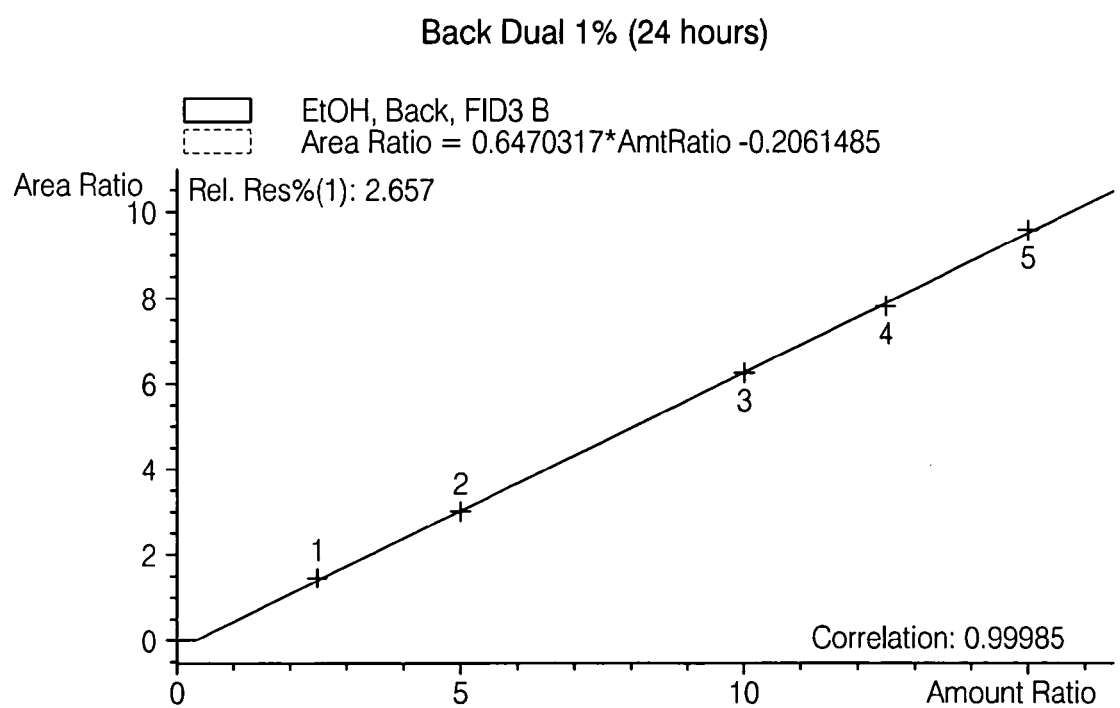
Figure 8C:
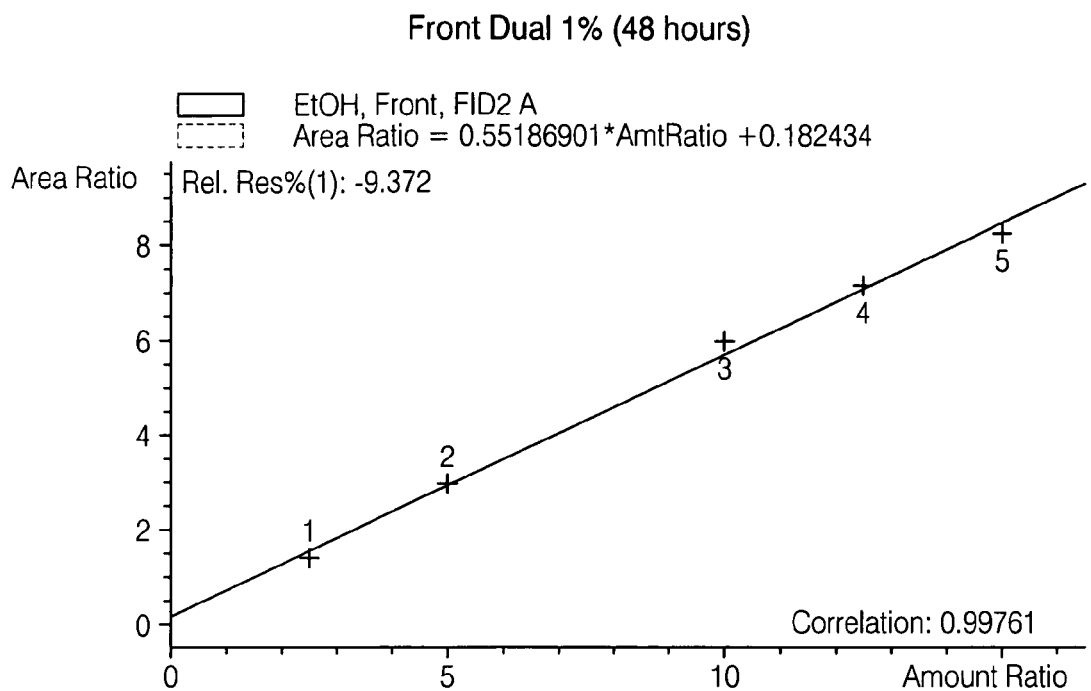
Figure 8D:
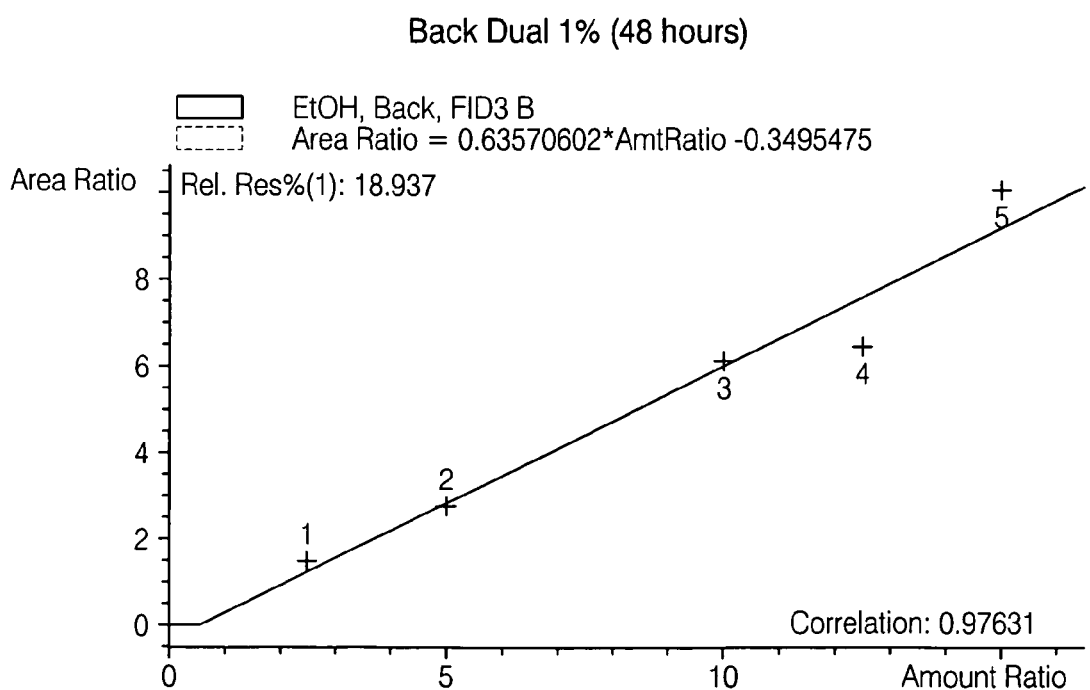
Figure 8E:
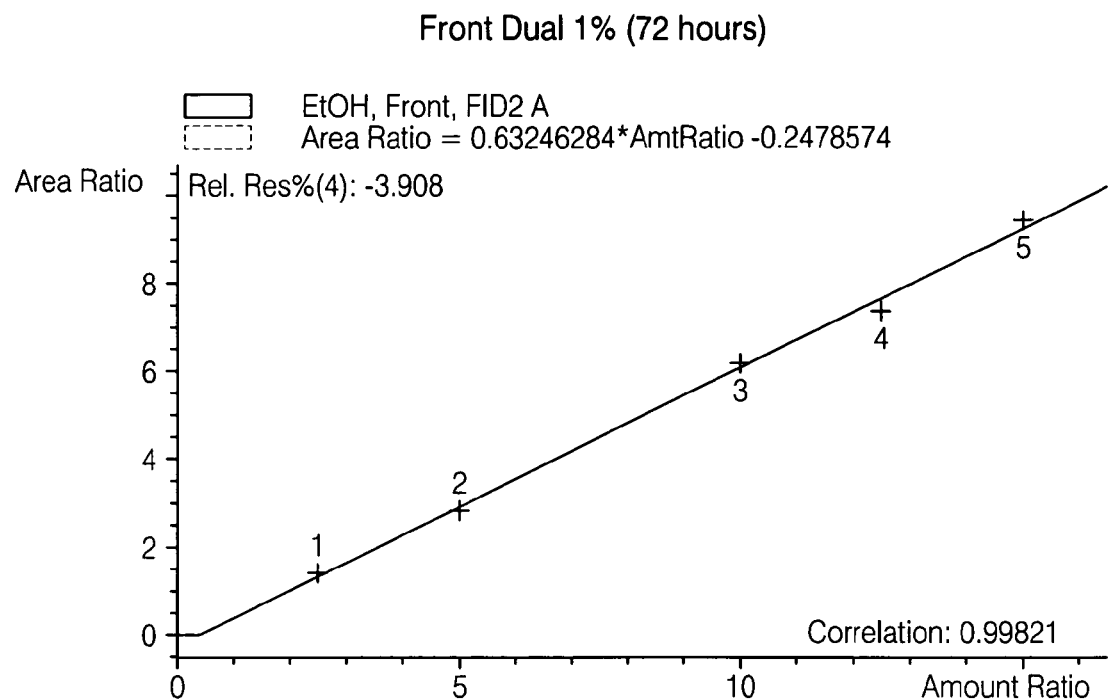
Figure 8F:
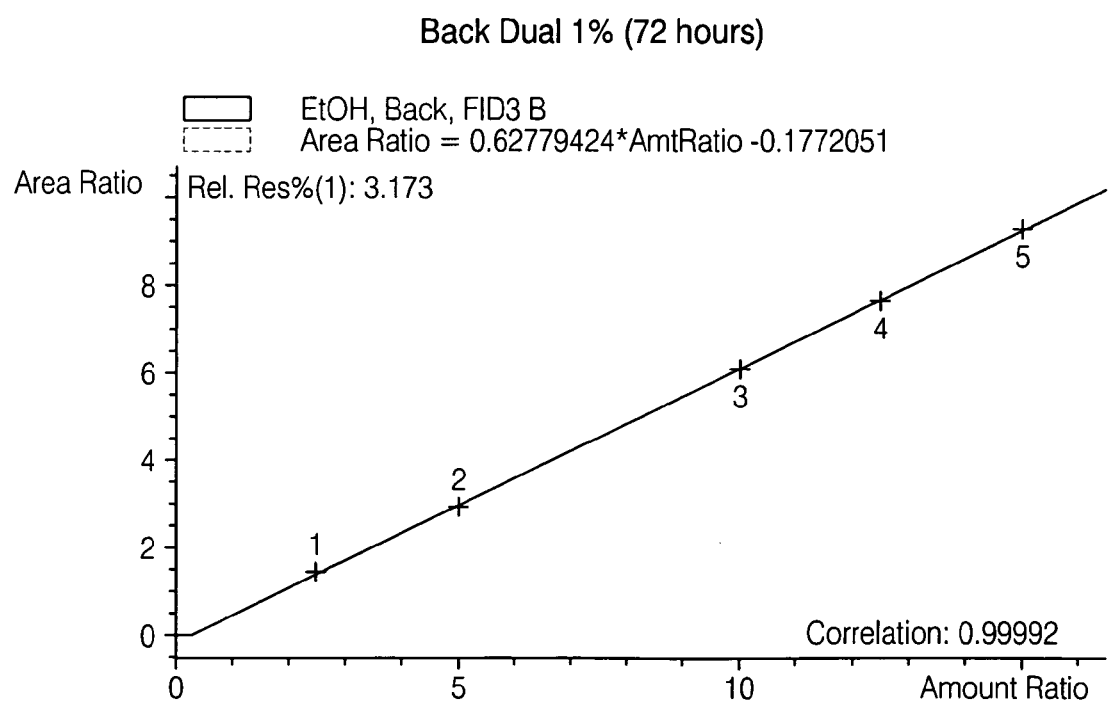
Figure 8G:
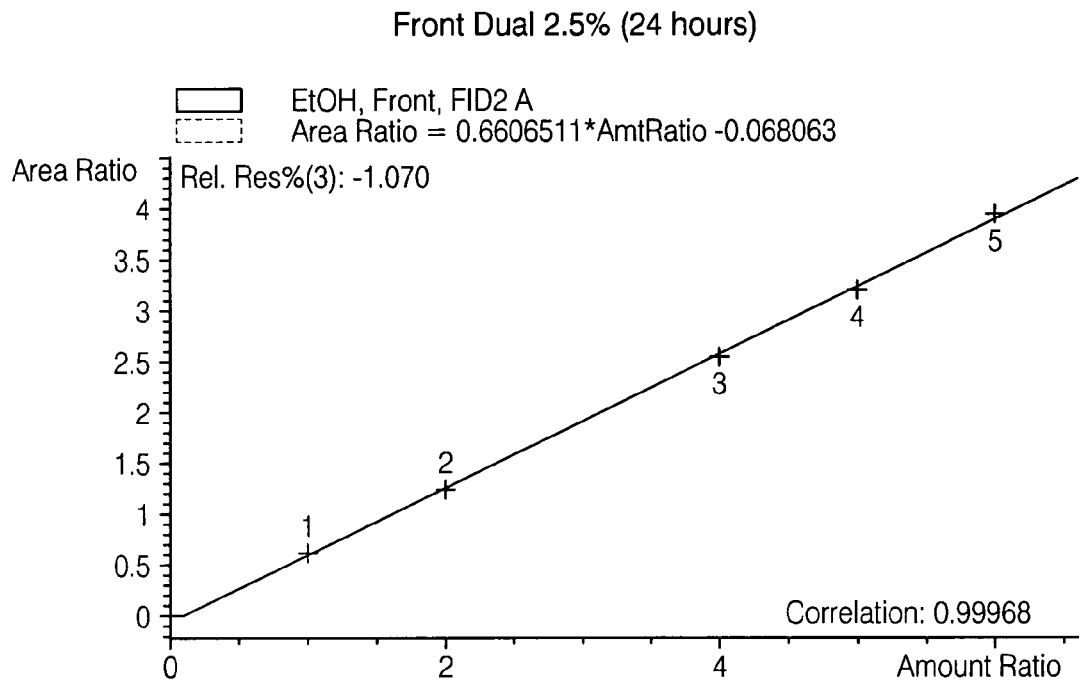
Figure 8H:
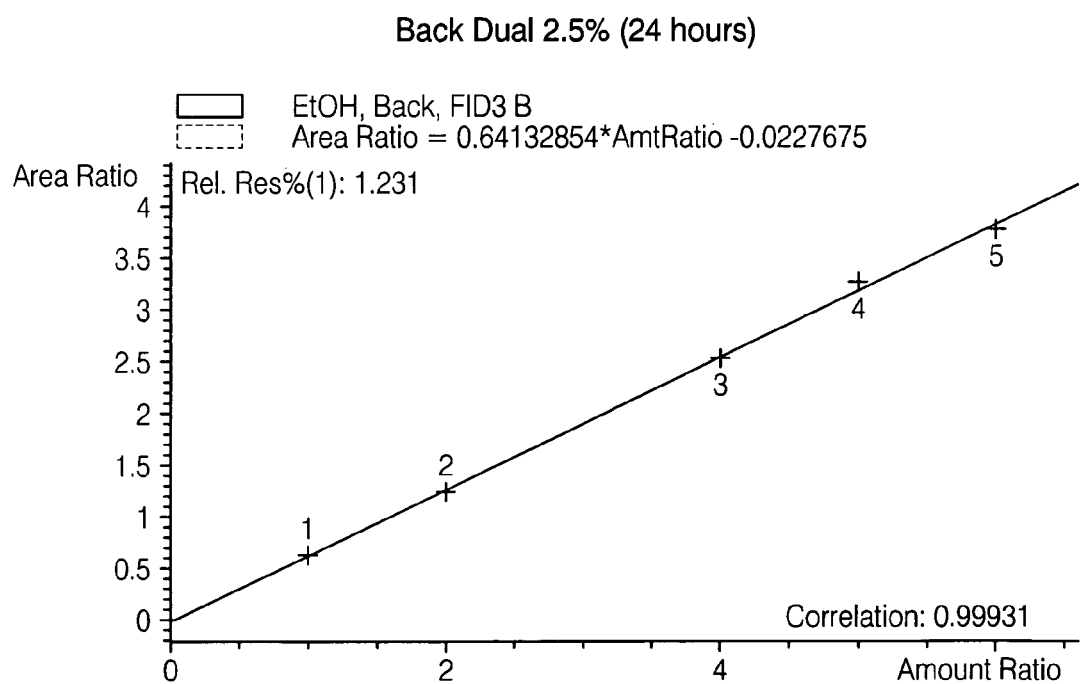

FIG. 1 illustrates a schematic representation of a system 100 used to calibrate for a near infrared analytical testing device configured to screen for ethanol production yield of an ethanol-producing material. For example, such a system may be used to build a calibration model for evaluating ethanol yield in biological materials such as, for example, seed (e.g., corn kernels), stover (plant and cob material), flour, and raw starch. In some embodiments, the system may be fully automated such that each component is in communication with at least one other component and operated by a controller device, without the need of a technician to move the sample between components. FIG. 2 is a flow chart illustrating a method 200 of calibrating for a near infrared analytical testing device configured to screen for ethanol production yield of an ethanol-producing material.

In one embodiment, to build the calibration model, a sample of the biological material is provided for processing by the system 100. A first analytical testing device 110 may be configured to interact or otherwise probe the sample material. In one instance, the first analytical testing device comprises an NIR spectrometer device configured to optically probe the sample material. The NIR spectrometer device may be configured to both transmit NIR energy in the direction of the sample material and receive reflected electromagnetic energy via fiber optics or other components, wherein such fiber optics or other components are in communication with an NIR processor portion. In one instance, the NIR spectrometer device may be a stand alone system with integrated computer software that can be operated to generate NIR energy of desired wavelengths, transmit them through a fiber optic, and collect reflected NIR energy, direct it through a fiber optic back to a processor portion where it can be recorded and analyzed. Selecting NIR energy, transmitting it to an item under analysis, collecting/detecting reflected or transmitted NIR from the object under analysis, and recording and processing collected NIR energy are well known to one of skill in the art, as well as operation of such machines. According to embodiments of the present invention, the method disclosed herein may comprise the step 210 of collecting a first signal. That is, the collected electromagnetic energy may be converted into a first signal capable of being recorded and displayed on a display device (e.g., a computer monitor) as two-dimensional spectra associated with the particular sample material being probed. As such, various characteristic parameters of the sample material may be discerned from the spectral data. More particularly, a characteristic parameter associated with enabling evaluation of the ethanol yield for a biological material having a substantially similar composition to the sample material may be determined. That is, the characteristic parameter may be used in characterizing the ethanol yield of a biological material to be analyzed.

In some instances, the sample material may be in a ground form such as flour or raw starch. In such instances, the NIR analysis by the first analytical testing device 110 may be completed on the sample material to determine the first signal associated therewith. However, in other instances, the sample material received may be in a non-ground form such as agricultural seed and stover (plant and cob material). In some instances, the non-ground sample material may be subjected to NIR analysis so as to determine spectra and associated characteristic parameters of the sample material in a non-ground state. In this regard, a calibration model may also be built that is used to evaluate ethanol yield without the need to grind the sample material for analysis, thereby reducing time and cost in the determination of ethanol yield for a particular sample material. Nonetheless, the sample material may still be ground and analyzed for more accurately building the calibration model.

Accordingly, an initial step in the calibration process may include a pretreatment or "grinding" step 205. Plant material can be initially processed by a variety of milling methods including but not limited to wet milling, dry milling, dry grinding, cracking, coarse grinding, fine grinding, fractionating, mixing, flaking, steam flaking, rolling or chopping. For example, plant material, such as kernels of corn, can be ground with a ball mill, a roller mill, a hammer mill, or another mill known for grinding plant material for the purposes of particle size reduction. The use of emulsion technology, rotary pulsation, and other means of particle size reduction can be employed to increase surface area of plant material while raising the effectiveness of flowing the liquefied media. To improve throughput and efficiency, the type of device used to process the plant material should be simple to use and simple to clean between grinding of successive samples.

The corn wet milling process separates corn into its four basic components: starch, germ, fiber and protein. There are four basic steps to accomplish this process. First the incoming corn is steeped to begin hydrolyzing the starch and breaking the protein bonds. The next step in the process involves a coarse grind to separate the germ from the rest of the kernel. The remaining slurry consisting of fiber, starch and protein is finely ground and screened to separate the fiber from the starch and protein. The starch is separated from the remaining slurry. The processed plant material can be referred to as being or including "raw starch."

In dry milling, the corn is combined with water in a brief tempering process prior to grinding the corn to a flour. The ground corn flour is then fractionated into bran, germ and grits (starchy fractions).

In dry grinding, the entire corn kernel or other starchy grain is first ground into flour, which is referred to in the industry as "meal" and processed without separating out the various component parts of the grain. The meal is slurried with water or backset to form a "mash."

Thus, it is envisioned that embodiments of the invention can be used in conjunction with any milling technique (including, but not limited to, wet milling, dry milling, dry grinding, cracking, coarse grinding, fine grinding, fractionating, mixing, flaking, steam flaking, rolling or chopping) to prepare the sample material for analysis by the first analytical testing device 110 for collecting the first signal. However, it is also envisioned that plant material that has been minimally processed or is unprocessed can be used in the methods disclosed herein. In a preferred embodiment, the plant material may be ground with a grinding unit 105 such as, for example, a disc mill grinder, as known to one of skill in the art.

The starting amount of plant material necessary for the systems and methods disclosed herein will vary, but it will generally be significantly less than the amount of starting material necessary to evaluate ethanol production in a full-scale conversion process. In fact, an advantage of the present invention is that model parameters can be evaluated when the availability of starting material is limited. In some embodiments, the amount of processed or unprocessed plant material used in a liquefaction step is less than about 10 grams, less than about 9 grams, less than about 8, 7, 6, 5, 4, 3, 2, or less than about 1 gram of material.

As discussed previously, NIR analysis with the first analytical testing device 110 may be implemented after the pretreatment process if the sample material is received in a non-ground form. After NIR analysis to collect the first signal with the first analytical testing device 110, the sample material may then be directed to a drying unit 120 for the step 220 of drying the sample material to a substantially standard or terminal moisture level. That is, plant material useful in the calibration process disclosed herein is typically dried prior to starch conversion. Any conventional drying technique can be used to achieve the desired standard moisture level. For example, drying may be accomplished either by specifically designed dryers operated on location. Also, commercial dryers are available in many forms, the most common of which are rotary kilns and shallow fluidized bed dryers. In a preferred embodiment, the sample material may be dried in a desiccating cabinet to drive the moisture of the sample to a substantially standard level. In this manner, a plurality of sample materials may be dried simultaneously, thereby improving efficiency and increasing throughput of the calibration process.

As mentioned previously, the processed or unprocessed plant material is driven to a desired moisture content prior to a liquefaction step. That is, the plant material may be driven to a predetermined and substantially standard moisture level. In one embodiment, the plant material is driven to a moisture content of less than about 20% (by weight), less than about 18%, less than about 15%, less than about 14%, less than about 13%, less than about 12%, less than about 11%, less than about 10%, less than about 9%, less than about 8%, less than about 7%, less than about 6%, or less than about 5% moisture. Drying all samples to a terminal moisture content prior to liquefaction eliminates the need to recalculate ethanol content based on the moisture level, thus increasing the efficiency of the process and accuracy of the ethanol measurement. In a preferred embodiment, the "terminal moisture" is intended to be a moisture content of between about 5% and 8% by weight of the plant material. Furthermore, the moisture content may be any predetermined level, provided that the moisture level is within a moisture level range among the various samples. That is, in some instances, the samples used in the calibration process may have a relatively high moisture level as long as the samples are within a predetermined range of moisture levels. For example, each sample may be driven to about a 20% moisture level, wherein the moisture level for each sample is within 1.5% of each other. In a preferred embodiment, the moisture level range may be about 1.5% (i.e., the terminal moisture level for each sample is within a 1.5% moisture level of each other).

In the methods of the present invention, all samples are driven to a particular moisture content/level (e.g., terminal moisture) using the drying unit 120 such as, for example, a drying cabinet or similar device capable of maintaining a relative humidity within the range of the desired moisture content. The use of a drying cabinet eliminates the need to perform moisture analysis on each individual sample, which also increases the efficiency of the method. In one embodiment, the relative humidity (RH) of the drying cabinet (i.e., "desiccating" cabinet) is maintained from about 5% to about 20%, or any range in between 5% and 20% including, for example, from about 5%, 6%, 7%, 8%, 9%, 10%, 11%, or 12% to about 13%, 14%, 15%, 16%, 17%, 18%, 19%, or 20% RH.

To facilitate drying of the samples, the temperature of the drying cabinet is maintained at about 20° C. to about 35° C., or any range in between about 20° C. and about 35° C. including, for example, about 21° C., about 22° C., about 23° C., about 24° C., about 25° C., about 26° C., about 27° C., about 28° C., about 29° C., about 30° C., about 31° C., about 32° C., about 33° C., or about 34° C. It is also envisioned that the moisture content of the starch-containing plant material, as well as the temperature at which this moisture content is achieved, may be modeled using the system and/or method disclosed herein.

After driving the moisture of the sample material to a substantially standard level, the sample material may be analyzed again using the first analytical testing device 110. That is, an NIR analysis may again be performed on the dried sample material. In this manner, the calibration method disclosed herein may comprise the step 230 of collecting a second NIR signal, which in some instances may be collected and displayed on a display device (e.g., a computer monitor) as two-dimensional spectra associated with the particular sample material being probed. As such, various characteristic parameters of the sample material may be discerned from the spectral data. More particularly, a characteristic parameter associated with enabling evaluation of the ethanol yield for a biological material having a substantially similar composition to the sample material may be determined.

In various embodiments, after drying of the processed or unprocessed samples and the second NIR analysis, a specific amount of each sample may be weighed in a moisture-controlled glove box preferably using an automated sample-dispensing unit. The RH of the glove box may be maintained from 0-20%, and a dry inert gas (e.g., nitrogen or helium) may be used in the glove box. The sample-dispensing unit may increase throughput and the use of the glove box may limit exposure of the samples to atmospheric moisture. The use of the glove box may also limit interaction of the user with the plant material, reducing the probability of an allergic reaction.

Embodiments of the present invention may further comprise processing the dried sample material, wherein the method disclosed herein comprises a step 240 of fermenting the sample material with a fermentation unit 130. The step 240 of fermenting may comprise preparation of the sample for fermentation. In some instances, processing may further involve the hydrolysis of starch, often mediated by one or more starch-degrading enzymes. The term "hydrolysis" is defined as a chemical reaction or process in which a chemical compound is broken down by reaction with water. The starch digesting enzymes hydrolyze starch into smaller units as previously described. Typical corn-to-ethanol conversion processes comprise liquefying an aqueous slurry of starch-containing plant material in the presence of one or more starch-degrading enzymes, e.g., α-amylase enzymes. The term "slurry" refers to a mixture of starch or a starch-containing material (e.g., milled corn) and an aqueous component, which can include, for example, water, deionized water, or a process water (i.e., backset, steam, condensate), or any combination thereof. The addition of water, enzyme, or other necessary nutrients or antibiotics to the plant material is typically performed using an automated dispensing unit, e.g., a robotic pipetting device. Use of this type of automated dispensing unit reduces the variability associated with hand-held devices such as pipetters, while also increasing throughput.

The liquefaction reaction involves heating a combination of ground grain and water beyond the grains' gelatinization point under slightly acidic conditions in the presence of an enzyme that will hydrolyze the linkage between the glucose units rendering a complex mixture of dextrins, sugars and other retrograde products. In order to facilitate wetting or mixing of the aqueous slurry, the liquefaction process can include an initial step of holding the slurry in a container (i.e., a pre-slurry container) for a period of time prior to the heating step. As used herein the terms "liquefaction," "liquefy," "liquefact," and variations thereof refer to the process or product of converting starch to soluble dextrinized substrates (e.g., smaller polysaccharides). Liquefact can also be referred to as "mash."

The methods used for liquefaction of an aqueous slurry of starch-containing plant material vary depending, in part, on the nature of the starch-degrading enzymes used in the process as well as the intended downstream use of the intermediate and end products. The steps can involve a single liquefaction step, or may involve a primary liquefaction, followed optionally by jet cooking and then a secondary liquefaction. The term "secondary liquefaction" refers to a liquefaction process that takes place after an initial period of liquefaction or after a jet cooking step of a multi-stage liquefaction process.

The conditions under which each step is performed also depends on the nature of the enzymes employed. For example, various starch-degrading enzymes have different degrees of thermostability and different requirements for pH. The steps should be performed under conditions sufficient for each type of starch-degrading enzyme employed in the process to hydrolyze the starch-containing plant material.

A common enzymatic liquefaction process involves adjusting the pH of a starch slurry to the pH optimum of the starch-degrading enzyme(s) employed in the methods, with the addition of calcium hydroxide, sodium hydroxide or sodium carbonate. The addition of calcium hydroxide has the advantage of also providing calcium ions which are known to stabilize certain starch-degrading enzymes against inactivation.

In another variation to the liquefaction process, a starch-degrading enzyme (e.g., α-amylase) is added to the starch suspension, the suspension is held at a temperature of 80-100° C. to partially hydrolyze the starch granules, and the partially hydrolyzed starch suspension is heated to temperatures in excess of about 105° C. to thoroughly gelatinize any remaining granular structure. After cooling the gelatinized starch, a second addition of the enzyme can be made to further hydrolyze the starch.

Yet another variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. A practice in the art is to undertake enzymatic liquefaction at a lower temperature when using the dry milling process.

In some embodiments, jet cooking could be desired. Thus, in some embodiments, the process further comprises a jet cooking step following the heating step. In some embodiments, the jet cooking comprises heating the slurry to a temperature ranging from about 90° C. to about 120° C. for a period of time ranging from about 3 minutes to about 15 minutes.

Following gelatinization, the starch solution may be held at an elevated temperature in the presence of a starch-degrading enzyme until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Fermentable sugar can be lost during high temperature, long hold times, and the use of only mildly acidic pH conditions. These losses can be attributed, at least in part, to Maillard reactions between a reducing end on the carbohydrate and an amino compound (e.g., ammonia or a protein). The Maillard reactions are known to be temperature, pH, and time dependent. Thus, various parameters can be modeled in the liquefaction step to achieve optimal starch-to-ethanol conversion.

At each step, the process can be modeled for a pH that is optimal for the particular enzyme(s) being employed in that step. In some embodiments, this slurry has a pH of between about 3.8 and about 5.2, including about 4.0, about 4.2, about 4.4, about 4.6, about 4.8, and about 5.0. In some embodiments, the pH is about 4.8. Reducing the pH from the 5.8 typical for liquefaction to a lower pH (e.g., between 5.2 and 3.8) should decrease the amount of Maillard reaction products.

In one embodiment, the process of starch liquefaction is modeled at a low pH, for example, the natural pH of a slurry comprising a milled starch-containing plant material and water. In this modeling, the starch liquefaction is performed at a lower pH, therefore no pH adjustment is necessary, either as part of liquefaction step or at any point during an ethanol production process involving a liquefaction step (i.e., throughout the combination of liquefaction, saccharification, and fermentation steps used to produce ethanol). Thus, no pH-adjusting materials (e.g., bases or salts) are added to the slurry.

The heating step of the liquefaction process can be modeled to involve the use of temperatures below those used during conventional liquefaction processes (e.g., below about 95° C. to 120° C.). In some embodiments, the liquefaction temperature ranges from about 60° C. to about 90° C. In some embodiments, the liquefaction temperature ranges from about 80° C. to about 90° C. In other embodiments, the liquefaction does not include a jet-cooking step. In some embodiments, the liquefaction does not include a secondary liquefaction step. Thus, the presently disclosed liquefaction method, in some embodiments, involves a single heating step, or no heating step at all. The temperature can be chosen to be compatible with thermostable glucoamylases, such as those derived from *Thermomyces lanuginosus* (i.e., *Thermomyces lanuginosus* glucoamylase).

Decreasing the time the slurry is held at high temperature should also decrease undesired degradation reactions. Thus, in various embodiments, the period of time for each liquefaction step can be less than about 180 minutes. In some embodiments, the period of time for each liquefaction step ranges from about 2 minutes to about 200 minutes, including from about 5, about 10, about 15, about 20, about 25, about 30, about 11, about 12, about 13, about 14, about 15, about 16, about 17, about 18, about 19, about 35, about 40, about 45, about 50, about 60, about 70, about 80, about 90, about 100, about 100, about 110, about 120, about 130, about 140, about 150, about 160, about 170, about 180, or about 190 minutes. In some embodiments, the period of time ranges from 60 minutes to about 150 minutes. It is envisioned that the period of time for each liquefaction step can be modeled for any period of time.

In various embodiments of the invention, each of the liquefaction steps may be performed in a convected oven set at the desired temperature. Performing liquefaction in the oven eliminates the space requirements needed for water baths, increases throughput and reduces the risk of exposure of the operator to hot water. Performing the liquefaction in a single oven may also reduce the temperature variation that is present between and within conventional water baths. This technique is successfully used with the small-volume headspace vials since the mass transfer of heat is greatly reduced with the small liquefacts. It will be understood that use of this technique with larger liquefact volumes will require longer residence times in the liquefaction oven.

An optional step in the starch-to-ethanol conversion process involves saccharification of the starch liquefact. As used herein, the terms "saccharification" and "saccharifying" refer to the process of converting polysaccharides to dextrose monomers using enzymes. Saccharification can specifically refer to the conversion of polysaccharides in a liquefact. Saccharification products are, for example, glucose and other small (low molecular weight) oligosaccharides such as disaccharides (a DP2) and trisaccharides (a DP3). The saccharification step can include adding one or more starch-degrading enzymes to the starch liquefact during liquefaction (simultaneous liquefaction and saccharification, SLS) or after liquefaction. In some embodiments, the additional starch-degrading enzymes include glucoamylase.

The amount of glucoamylase employed in the present process can vary according to the mixture of dextrins present in the starch liquefact. For example, if the starch liquefact is high in concentration of fermentable, small sugars, less glucoamylase might be needed.

The saccharification process can further include a heating step, wherein the starch liquefact comprising additional starch-degrading enzymes (i.e., the saccharification mixture) is heated to a temperature (e.g., a temperature that allows for optimal activity for the enzymes employed) for a period of time. For example, the starch liquefact can be heated in the presence of an additional starch-degrading enzyme (e.g., glucoamylase) for a period of time from about 5 minutes to about 90 minutes at a temperature from about 60° C. to about 75° C. The temperature can be chosen to be compatible with thermostable glucoamylases, such as those derived from *Thermomyces lanuginosus* (i.e., TlGA).

In some embodiments, the heating step effects complete saccharification of the slurry. Thus, in some embodiments, approximately 100% of the glucose expected from hydrolysis of the starch in the slurry is produced during the heating step. In some embodiments, the heating step effects partial saccharification of the slurry. For example, heating can lead to a mixture containing at least some glucose and some larger dextrins.

In some embodiments, the process can include a separate second saccharification step. For example, the process can comprise heating the mixture containing glucose to a second temperature for a second period of time, thereby effecting complete saccharification of the mixture. This second heating step can include the addition of additional enzyme, e.g., additional glucoamylase.

In some embodiments, the mixture from a partial SLS process can be used in a fermentation wherein additional saccharification can take place during fermentation. Thus, in some embodiments both additional enzymes and yeast can be added to the mixture, thereby producing additional glucose and producing ethanol. In some embodiments, the glucose of the presently disclosed process can be used to produce an end product selected from the group consisting of an alcohol, lactic acid, an amino acid, fructose, citric acid, propanediol, DDG, DDGS, or a combination thereof.

The glucose produced from a complete simultaneous liquefaction and saccharification process can also be modeled. In addition to glucose, the heated mash can comprise additional materials, such as oil, protein and fiber by-products of the simultaneous liquefaction and saccharification process. These materials can also have economic value and can be recovered as well.

Subsequent modeling of fermentation of a partially saccharified mixture can be advantageous, in that it allows for modeling the control of the initiation, rate, and/or extent of fermentation activity during a SSF process. In particular, the quantity of different starch-containing plant materials and or enzymes can be adjusted to provide a suitable amount of glucose to enhance the survival of yeast during a subsequent fermentation of the mixture resulting from the simultaneous liquefaction and saccharification process. The amount of glucose being fed into a fermentation process can also affect the quality of co-products of the fermentation process, including dried distiller grain and dried distiller grain and solubles.

As discussed previously, one or more steps of the conversion process employs one or more starch-degrading enzymes, and the type, amount, and source of enzymes can be modeled using the platform described herein. The term "starch-degrading enzyme" includes any enzyme that can catalyze the transformation of a starch molecule or a degradation product of a starch molecule. Starch-degrading enzymes can be added to the starch hydrolysis process as either a purified or semi-purified enzyme preparation (i.e., liquid or dry enzyme) added when the processed plant material is mixed with water or can be delivered by using transgenic plant material expressing the starch-degrading enzyme as described in US patent application US2003/0135885 (herein incorporated by reference in its entirety). Transgenic plant material expressing a starch-degrading enzyme can be combined with at least one other starch-containing plant material to form an admix such that the transgenic plant material delivers an appropriate amount of starch-degrading enzyme to perform the starch hydrolysis process.

The different plant materials may be combined by one or more process, including but not limited to, wet milling, dry milling, dry grinding, cracking, coarse grinding, fine grinding, fractionating, mixing, flaking, steam flaking, rolling and chopping. The mix can be formed by mixing dry plant materials from different starch-containing plants together before wetting with the aqueous solution. It is also possible to form a mash by adding the different starch-containing plant materials sequentially or simultaneously to a vessel while an aqueous solution is being added. Any suitable mixing method can be used, including any suitable manual or mechanical mixing method that can be used in conjunction with the pre-slurry, slurry and liquefaction. However, to increase consistency and speed of the process, a high speed/high throughput shaker may be typically used. The utilization of this type of shaker reduces the variation associated with shaking samples by hand, using multiple stir plates or using multiple orbital shakers.

Starch-degrading enzymes suitable for the present invention include starch-degrading or isomerizing enzymes including, for example, $\alpha$-amylase (EC 3.2.1.1), endo or exo-1,4- or 1,6-$\alpha$-D-glucoamylase, glucose isomerase, $\beta$-amylases (EC 3.2.1.2), $\alpha$-glucosidases (EC 3.2.1.20), and other exo-amylases; starch debranching enzymes, such as isoamylase (EC 3.2.1.68), pullulanase (EC 3.2.1.41), neo-pullulanase, iso-pullulanase, amylopullulanase and the like; glycosyl transferases such as cyclodextrin glycosyltransferase and the like. Starch-degrading enzymes can be used in conjunction with other enzymes that can facilitate the release of starch from plant tissue. Starch-degrading enzymes can be used in conjunction with cellulases such as exo-1,4-$\beta$-cellobiohydrolase (EC 3.2.1.91), exo-1,3-$\beta$-D-glucanase (EC 3.2.1.39), hemicellulase, $\beta$-glucosidase and the like; endoglucanases such as endo-1,3-$\beta$-glucanase (EC 3.2.1.6) and endo-1,4-$\beta$-glucanase (EC 3.2.1.4) and the like; L-arabinases, such as endo-1,5-$\alpha$-L-arabinase (EC EC 3.2.1.99), a-arabinosidases (EC 3.2.1.55) and the like; galactanases such as endo-1,4-$\beta$-D-galactanase (EC 3.2.1.89), endo-1,3-$\beta$-D-galactanase (EC 3.2.1.90), 1-galactosidase, a-galactosidase and the like; mannanases, such as endo-1,4-$\beta$-D-mannanase (EC 3.2.1.78), β-mannosidase (EC 3.2.1.25), a-mannosidase (EC 3.2.1.24) and the like; xylanases, such as endo-1,4-1-xylanase (EC 3.2.1.8), β-D-xylosidase (EC 3.2.1.37), 1,3-β-D-xylanase, and the like; pectinases and phytases. In some embodiments, the starch-degrading enzyme is α-amylase, pullulanase, α-glucosidase, glucoamylase, amylopullulanase, glucose isomerase, or combinations thereof.

The starch-degrading enzyme or combination thereof can be modeled based on the desired starch-derived end product, the end product having various chain lengths based on, e.g., a function of the extent of processing or with various branching patterns desired. For example, an α-amylase, glucoamylase, or amylopullulanase can be used under short incubation times to produce dextrin products and under longer incubation times to produce shorter chain products or sugars. A pullulanase can be used to specifically hydrolyze branch points in the starch yielding a high-amylose starch, or a neopullulanase can be used to produce starch with stretches of α-1,4 linkages with interspersed α-1,6 linkages. Glucosidases can be used to produce limit dextrins, or a combination of different enzymes can be used to make other starch derivatives. In some embodiments, a glucose-isomerase can be selected to convert the glucose (hexose) into fructose.

Alpha-amylase refers to an enzyme which cleaves or hydrolyzes internal α (1-4) glycosidic bonds in starch to produce α 1-2 bonds, resulting in smaller molecular weight maltodextrins. These smaller molecular weight maltodextrins include, but are not limited to, maltose, which is a disaccharide (i.e., a dextrin with a degree of polymerization of 2 or a DP2), maltotriose (a DP3), maltotetrose (a DP4), and other oligosaccharides. The enzyme α-amylase (EC 3.2.1.1) can also be referred to as 1,4-α-D-glucan glucanohydrolase or glycogenase. A variety of α-amylases are known in the art and are commercially available. An α-amylase can be from any organism including plant, fungi, and bacteria, and can be expressed in transgenic plants. The α-amylase can be thermostable. The alpha-amylase can be 797GL3.

Glucoamylase (also known as amyloglucosidase) refers to the enzyme that has the systematic name 1,4-α-D-glucan glucohydrolase (E.C. 3.2.1.3). Glucoamylase removes successive glucose units from the non-reducing ends of starch. A variety of glucoamylases are known in the art and are commercially available. For example, certain glucoamylases can hydrolyze both the linear and branched glucosidic linkages of starch, amylose, and amylopectin. Glucoamylase can be from any organism including plant, fungi, and bacteria, and can be expressed in transgenic plants. The glucoamylase can be thermostable.

The type, amount, and/or source of starch-degrading enzyme can be modeled using the methods of the present invention. For example, enzymes having different substrate specificities, temperature optima, thermal tolerance, stability, pH requirements, and the like can be tested alone or in various combinations for improvements in the starch-to-ethanol conversion process. In one embodiment, the amount of glucoamylase is modeled according to the mixture of dextrins present in the starch liquefact. For example, if the starch liquefact is high in concentration of fermentable, small sugars, less glucoamylase might be needed.

In some embodiments, the starch-degrading enzyme(s) can be provided in the slurry as transgenic plant material expressing one or more starch-degrading enzymes, may be provided as a purified or semi-purified enzyme preparation and exogenously added to the slurry, or may be provided in any combination thereof. Where multiple starch-degrading enzymes are employed, the slurry may comprise an admixture of a first starch-containing plant material expressing at least a first starch-degrading enzyme, and a second starch-containing transgenic plant material that expresses a second starch-degrading enzyme. Alternatively, the different starch-degrading enzymes can be expressed from a single variety of plant that expresses each starch-degrading enzyme through transformation or breeding. The admixture may further comprise starch-containing plant material that does not express any starch-degrading enzyme. Likewise, the admixture may comprise transgenic starch-containing plant material expressing only one starch-degrading enzyme (where the second starch-degrading enzyme is added exogenously to the slurry) or may consist only of starch-containing plant material that does not express a starch-degrading enzyme (where each starch-degrading enzyme is added exogenously to the slurry). The slurry can further comprise an aqueous solution (e.g., water, de-ionized water, backset (i.e., stillage), etc.).

Where one type of starch-degrading enzyme is provided as transgenic plant material, and another type of starch-degrading enzyme is provided exogenously as a purified or semi-purified enzyme preparation, the initial liquefaction steps may be performed under conditions compatible with the transgenically-expressed starch-degrading enzyme. The exogenous starch-degrading enzyme can be added to the slurry during the initial liquefaction steps if the enzyme has similar thermostability and pH optimum characteristics as the transgenically-expressed starch-degrading enzyme.

Alternatively, the exogenous starch-degrading enzyme can be added in a secondary liquefaction step. This secondary liquefaction step should be performed under conditions sufficient for the exogenous starch-degrading enzyme to hydrolyze the starch-containing material, which may or may not require adjustment of the pH and/or ion concentrations of the slurry.

Where two or more types of starch-degrading enzymes are added to the slurry exogenously, the liquefaction steps should be compatible with both types of enzymes, and may require separate liquefaction steps with adjustment of pH and/or ion concentrations between the steps. One of skill in the art will recognize that the pH, ion concentration, temperature, and length of time for each step can be optimized according to the type of starch-degrading enzyme(s) employed in the liquefaction as well as the products desired from the liquefaction. Likewise, the pH, ion concentration, temperature, and length of time for each liquefaction step can be modeled to improve production of ethanol and/or by-products or end products of the starch-to-ethanol conversion process. Exemplary, non-limiting liquefaction methods are provided elsewhere herein.

Following the preparation steps of liquefaction, saccharification, or SLS, the resulting hydrolyzed sugars and starch may be fermented with the fermentation unit 130. "Fermentation" or "fermenting" refer to the process of transforming sugars from reduced plant material to produce alcohols (e.g., ethanol, methanol, butanol, propanol); organic acids (e.g., citric acid, acetic acid, itaconic acid, lactic acid, gluconic acid, propionate); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Fermentation can include fermentations used in the consumable alcohol industry (e.g., beer and wine), dairy industry (e.g., fermented dairy products), leather industry, and tobacco industry. Thus, fermentation includes alcohol fermentation. Fermentation also includes anaerobic fermentations.

In one embodiment, the capacity and efficiency of the process may be improved by performing fermentation reactions in small, preferably single-use, vials (e.g., small-volume headspace vials, such as 20 ml headspace vials). Performing the fermentations in small-volume vials may significantly increase the number of simultaneous fermentation reactions that can be performed compared to methods using larger vessels. Accordingly, space requirements for the fermentations may be greatly reduced. Furthermore, single-use vials reduce the time and effort required to wash glassware.

The fermentation step 240 may be accomplished by any organism suitable for use in a desired fermentation step. Suitable fermenting organisms are those that can convert DP1-3 sugars, especially glucose and maltose, directly or indirectly to the desired fermentation product (e.g., ethanol, propanol, butanol or organic acid). Fermenting can be effected by a microorganism, such as fungal organisms (e.g., yeast or filamentous fungi). The yeast can include strains from a *Pichia* or *Saccharomyces* species. The yeast can be *Saccharomyces cerevisiae*. Bacterial can also be used in a fermentation process. Bacteria include but are not limited to species from *Acetobacter*, engineered *E. coli, Clostridium, Acidofilous* or *Lactobacter*. The selection of yeast can be modeled using the methods disclosed herein. Further, the amount of yeast employed can be modeled to effectively produce a desired amount of ethanol in a suitable time.

In some embodiments, the fermentation step involves a simultaneous saccharification and fermentation (SSF) step. In yet another embodiment, the starch-containing plant material may be used in raw starch fermentation. In the raw starch fermentation, the starch is not liquefied before enzymatic hydrolysis, and the hydrolysis is carried out at a temperature below gelatinization simultaneously with the fermentation process.

In some embodiments, the fermentation step comprises adding a solution of yeast to the cooled starch liquefact or raw starch and agitating the cooled starch liquefact at a temperature from about 28° C. to about 35° C. for a period of time sufficient for conversion of a sufficient quantity of the sugars to ethanol, e.g., from about 12 to about 72 hours. In some embodiments the yeast is Ethanol Red yeast.

The saccharification and/or fermentation mixture can include additional ingredients to increase the effectiveness of the process and it will be understood that any of these ingredients can be modeled to improve the starch-to-ethanol conversion process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like. In some embodiments, the process comprises adding one or more reagents from the group consisting of an additional starch-degrading enzyme, a yeast extract, an antibiotic, and yeast to the starch liquefact.

In an embodiment, fermentation is conducted for about 12 to about 96 hours, for example from about 18 to about 72 hours, about 24 to about 72 hours, about 48 to about 72 hours, or about 48 to about 96 hours. For example, fermentation can be conducted for about 12, about 18, about 24, about 30, about 36, about 42, about 48, about 54, about 60, about 66, about 72, about 78, about 84, about 90, or about 96 hours. In an embodiment, fermentation is conducted at a temperature of about 25° C. to about 40° C., or about 30° C. to about 35° C.

In some instances, to stop the fermentation process, the samples may be pasteurized in a convected oven set at 80-90° C. for a period of 40-60 minutes. The use of pasteurization limits exposure to acids used to stop the fermentation in a conventional process and eliminates corrosive acids from being injected into devices used to measure products of the conversion process. This technique is successfully used with the small-volume headspace vials since the mass transfer of heat is greatly reduced with the small ferments. It will be understood that use of this technique with larger fermentation volumes will require longer residence times in the pasteurization oven. Use of pasteurization is preferred over the alternative of not stopping the fermentation, which creates variation between fermentation times of samples being prepared for analysis.

As noted elsewhere herein, in some embodiments, the entire ethanol producing process can be modeled to have no pH adjustment. Thus, in some embodiments, no salts are added during saccharification and/or fermentation. Eliminating pH adjustments can reduce the costs of purchasing and storing chemicals and can reduce the salt content of the intermediates (e.g., glucose) produced. The elimination of calcium containing salts can reduce the formation of "beer stone" and the costs associated with its removal.

After the step 240 of fermenting the sample material, the sample material may be analyzed by a second analytical device 140 configured to implement the step 250 of collecting a reference measurement associated with fermentation properties, such as, for example, ethanol production (i.e., final ethanol concentration), associated with the sample material. As such, the fermentation properties may be correlated to the detected/measured NIR spectral data, as illustrated by step 260, so as to form a correlation between such spectral (i.e., the characteristic parameter) with the ethanol production yield. In this manner, the correlated data may be used to build a calibration model for an NIR spectrometer device such that the previously described procedure need not be carried out in order to evaluate the ethanol production yield of a biological material having a substantially similar composition as the sample material.

Thus, the reference measurement(s) may be correlated to the characteristic parameter to determine a plurality of calibration values used to build the calibration model. As such, within a device used to evaluate ethanol yield may be integrated a processor portion having a memory portion such that the calibration values may be recorded for a group of characteristic parameters, wherein this group enables evaluating ethanol yield in a biological composition having such detectable characteristic parameters. The characteristic parameter(s) being associated with the spectroscopic spectral data selected for each characteristic parameter to permit evaluation of the characteristic parameter in a biological composition from an infrared absorption spectrum, which can be generated on a sample of the biological composition. In this regard, spectral data from a biological material may be applied to the continuous spectrum produced by the first analytical testing device 110 to evaluate by automatic calculation the value of the characteristic parameter in the biological composition and, thus, evaluate ethanol yield based on the calibration values provided thereby.

The various calibration values are established for each characteristic parameter from sample material compositions in which the real value of the characteristic parameter is known, e.g. predetermined by physical-chemical measurement in a laboratory. The statistical correlation between the continuous spectra obtained for the various sample compositions and the known real values of each characteristic parameter may be determined from a statistical calculation made by means of a known statistical calculation program, in particular a statistical spectroscopic program such as that disclosed in U.S. Pat. No. 6,885,003 to Dubernet, incorporated herein by reference in its entirety.

Previously, the production of ethanol may have been monitored or the amount of ethanol measured using high-performance liquid chromatography (HPLC), which requires time-consuming sample preparation steps. As such, while the use of HPLC is not specifically excluded for measuring certain by-products or end products of starch-to-ethanol conversion, a preferred method for measuring ethanol production may be headspace analysis, preferably using gas chromatography. The "headspace" is the gas space in a vial above the sample. Headspace analysis is, therefore, the analysis of the components present in that gas. Headspace analysis makes use of the dynamic equilibrium existing at a given temperature and pressure between ethanol in liquid and vapor phases within the fermentation vial.

Headspace gas chromatography (HSGC) generally consists of a static or dynamic headspace gas sampling device, which may be manually operated or automated, and a gas chromatograph (GC) device. The ethanol concentration of the headspace air is determined by sampling a portion of the vial headspace and analyzing the headspace sample with a GC. This step may be typically performed automatically using an auto-sampling system. A representative fraction or the total amount of the volatile components is carried into the chromatographic column mounted in the oven of a gas chromatograph. In this manner, the reference measurement may be rapidly determined for the GC analysis such that the processing throughput of the sample material in regard to building the calibration model may be increased. In some instances, HPLC analysis of the sample material may be further carried out in a third analytical testing device 150 such that an additional/supplemental reference measurement may be obtained for quality control and/or, alternatively, for improving the calibration model by further correlating the spectral data of the sample material from the NW analysis with the supplemental reference measurement.

Several GC devices are commercially available, including devices with dual injectors for analysis of two samples at the same time. Dynamic headspace sampling devices usually preconcentrate a representative fraction or the total amount of the volatile components of the test sample in a trap. The representative fraction or the total amount of the preconcentrated volatile components of the test sample is then carried from the trap into the chromatographic column mounted in the oven of a gas chromatograph. A flow of carrier gas carries the volatile components through the chromatographic column where they are separated. The separated components enter a detector, which determines the concentration or mass flow of the components in the carrier gas.

Thus, a calibration model may be built by correlating the spectral data (and associated characteristic parameter) for a specific sample material with reference measurements of the same sample material to enable rapid evaluation of ethanol yield for a biological material having a composition similar to that of the sample material. That is, at least the steps of drying and fermenting the sample material would be unnecessary in making an evaluation as to the ethanol yield of a biological material, such as agricultural seed, upon receipt thereof, without the need to perform the laborious laboratory techniques described herein for determining ethanol yield, such as by HPLC. The disclosed system and method embodiments of the present invention are thus provided to efficiently build a calibration model for a testing device in which the calibration model is achieved through a high throughput process capable of rapidly processing any number of sample material to compile the spectral data and build the calibration model. That is, after calibration, the ethanol yield analysis of each biological composition may be obtained in a single automatic, simple and rapid step.

The following experiments are offered by way of illustration and not by way of limitation.

EXPERIMENTS

The invention is made up of a number of processes. Most of the experiments listed below followed this protocol unless noted otherwise in the experiment. The method steps may include a. grinding, b. drying corn flour, c. weighing flour, d. water, nutrient, antibiotic and enzyme addition, e. liquefaction, add fermentation cocktail, f. fermentation, stop fermentation, g. pasteurization, and h. headspace analysis via gas chromatography. The calculator for different components is based on g of dry flour and all liquefactions and fermentations are assembled accordingly. Therefore it is imperative that the percent moisture of corn flour be determined.

a) Grinding—standard disc mill grinder is used.
b) Drying corn flour—the corn flour is driven to a terminal moisture level in a desiccating cabinet. The RH of the moisture cabinet may be from 5 to 20%, with a temperature range of 20 to 35° C.
c) Weighing Flour—Corn flour is weighed in a moisture-controlled glove box using an automated flour-dispensing unit. The RH of the glove box is maintained from 0-20%.
d) Addition of water, nutrient, antibiotic and enzymes—Each of the components listed are dispensed using computer controlled, repeating, dispensing units. Dispensing ranges are from 10 ul to 10 ml
e) Liquefaction—performed at a temperature range of about 75 to 95° C. for about 1 to 2 hours.
f) Fermentation—performed in 30±5° C. growth chambers. Ferments are allowed to grow for 24, 48 and 72 hours.
g) Pasteurization—to stop the fermentation process, the samples are pasteurized in a convected oven set at 80-90° C. for a period of 40-60 minutes.
h) Headspace analysis via gas chromatography—to analyze the samples ethanol content headspace GC analysis is utilized. The sample is incubated at 45±5° C. for 1.5 to 1.8 minutes. A headspace sample is then removed with a 46±5° C. heated syringe. The syringe then is injected into a 250±5° C. injection port, with a split flow of 25:1. The sample components are separated on an Agilent DB-ALC1 column at an isothermic oven temperature of 75±5° C. with a column flow of 7.5±0.5 ml/min.

Experiment 1

Component Loss of Fermentation Components Due to Pasteurization Step in the HTS Fermentation Platform Research Objective
Research Hypothesis:
In order for the high throughput fermentation platform to provide accurate ethanol yield data, the ferment must be arrested prior to analysis. To arrest the ferment the yeast must be killed to prevent fermentation from occurring beyond the specific fermentation time point of interest. One way in which the yeast may be killed is to pasteurize the ferment, a method used in the brewing industry. Pasteurizing the ferments in the 20 ml headspace vials for a period of 45 minutes arrests the fermentation. Utilizing pasteurization as a method to kill the yeast may also cause loss of fermentation components due to evaporation. The hypothesis of this experiment is that the loss of any components due to evaporative loss is consistent across all headspace fermentation vials.

Technical Approach:

One-hundred and eight (108) fermentations are conducted in 20 ml headspace vials. The fermentation is divided into 3 treatment groups with 36 replications per treatment. Table 1 summarizes the treatments.

TABLE 1

Sample Matrix Design for the Measurement of Evaporative Weight Loss

| Treatment | # of Replications | Length of Fermentation (hours) |
|---|---|---|
| 1 | 36 | 24 |
| 2 | 36 | 48 |
| 3 | 36 | 72 |

A total of 108 headspace vials containing ferments are arrested after fermenting 24, 48 and 72 hours. The headspace vials containing ferment are weighed prior to the pasteurization step and immediately afterwards to determine the mass loss due to evaporation.

Materials and Methods

| | |
|---|---|
| Yellow dent corn | Perten 3600 Disc Mill |
| Perten DA7200 | Urea 1 g/2 ml Stock |
| VWR incubator | Sigma *A. niger* Glucoamylase |
| 20 ml headspace vials | Analytical balance |
| Tetracycline (10 mg/ml in 50% EtOH stock solution). | Ethanol Tech AYF 1177 |
| Genencor Spezyme Xtra | Ethanol Tech SLY Yeast |
| Growth chamber | Fluid Management 5G HD Mixer |
| Despatch Forced Convected Bench-top Oven | Mettler Toledo AB135-S/FACT Balance |

Yellow dent corn was ground using a Perten 3600 Disc Mill, on setting 0.

Moisture content of the flour was measured using a Perten DA7200.

The "Liquefaction Fermentation calculator" was used to determine the appropriate amounts of yellow dent corn flour, water, and alpha amylase (Genencor's Spezyme Xtra) to achieve 30% dry solids and placed into 108 headspace vials for liquefaction.

Liquefactions were carried out in the Despatch convected oven at 85° C. for 90 minutes. During liquefaction, the vials were mixed every 20 minutes using the 5G HD mixer.

After the liquefaction the samples were cooled to ambient temperatures.

The "Liquefaction Fermentation calculator" was used to determine the appropriate amounts of glucoamylase, nutrient, antibiotic, and yeast to add to each sample.

The vials were mixed once again using the 5G HD mixer.

The samples were placed in the 30° C. growth chambers and allowed to ferment for 24, 48 or 72 hours. A small hole should be punctured in each cap for ventilation during fermentation.

Ninety (90) microliters of n-propanol alcohol is added to each vial at the end of each fermentation period.

The mass of each vial was determined using the Mettler balance. The initial mass was recorded.

The vials were placed in the Despatch convected oven at 85° C. for 45 minutes to pasteurize the samples At the end of the 45 minute pasteurization the vials were removed from the oven and allowed to cool to ambient temperature.

The final mass of the vials was then determined and recorded. The change in mass was determined for each vial using the formula:

Mass Loss due to Pasteurization=$Mass_{(initial)}$−$Mass_{(final)}$

Results and Discussion

The loss of mass due to the pasteurization step was consistent across the 3 fermentation periods. The mean losses for each fermentation period are the following: a) 24 hour fermentation=7.7 mg, b) 48 hour fermentation=5.3 mg, and c) 72 hour fermentation=6.5 mg. A single factor ANOVA was used to compare the 3 sample sets. There was no significant difference found (P=0.60) in the loss of mass between the sample sets.

The results of this experiment clearly indicate that the loss of volatile components due to the pasteurization step is consistent across the three fermentation periods. Adjustments for evaporative mass loss do not need to be made to ethanol data collected across the three fermentation periods. The results of this experiment also indicate that the mean loss of volatile components due to the pasteurization step is <0.1% of the 9 g ferments utilized on the high throughput fermentation platform.

Experiment 2

Waxy Near Isogenic Inbred Lines (NILS) Study

Research Objective

Research Hypothesis:

This study hypothesizes that a near isogenic inbred line (NILS) of the waxy trait with 100% amylopectins will result in a faster accumulation of soluble dextrins as compared to non-waxy NIL corn, which in theory will result in a faster fermentation reaction in a high throughput dry grind process.

Technical Approach:

120 fermentations will take place in 20 ml headspace vials. The 120 fermentations are divided into 2 treatments with 10 reps per time point for 2 maize lines. The time points are 24, 48, and 72 hours. The 2 treatments are: 1) 30% solids and 3) 36% solids. Table Sample Matrix of Waxy Near-Isogenic Lines Study summarizes the treatment groups.

TABLE

Sample Matrix of Waxy Near-Isogenic Lines Study

| Maize Lines | Pedigree | Solids | Time Point | Reps | Total |
|---|---|---|---|---|---|
| Waxy NIL | C9RA | 30, 36 | 24, 48, 72 hours | 10/solid/time point | 60 |
| Non-waxy NIL | C9 | 30, 36 | 24, 48, 72 hours | 10/solid/time point | 60 |
| | | | | Project Total | 120 |

Work Plan:

The samples will be randomized in 1 day of fermentation (see Appendix B). Each sample will be fermented for 72 hours in the growth chamber at 30° C. At 24, 48, and 72 hours, samples will be prepared for ethanol analysis via GC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Genencor ® Spezyme Xtra | Ethanol Tech ® AYF1177 Nutrient |
| Distilled water | Tetracycline |
| Shaker | Oven |
| 20 ml headspace vials and caps | Growth Chamber |
| Analytical Balance | Powder handling system |
| Liquid handling system | Gas chromatography |

Moisture is measured on the sample using the Perten DA NIR7200.

Use the powder handling system to weigh 3 g of corn flour into each 20 ml headspace vial and cap each vial after weighing.

Use the "Dry-Grind Ethanol Calculator" and the moisture measured to determine the appropriate amounts of water and alpha amylase to achieve the necessary dry solids for each sample. Refer to Table Sample Matrix of Waxy Near-Isogenic Lines Study.

TABLE

Sample Matrix of Waxy Near-Isogenic Lines Study

| Maize Lines | Pedigree | Solids | Time Point | Reps | Total |
|---|---|---|---|---|---|
| Waxy NIL | C9RA | 30, 36 | 24, 48, 72 hours | 10/solid/time point | 60 |
| Non-waxy NIL | C9 | 30, 36 | 24, 48, 72 hours | 10/solid/time point | 60 |
| | | | | Project Total | 120 |

Dispense the liquids using the liquid handling system by piercing each vial cap.

Liquefactions are carried out in an oven at 85° C. for 90 minutes. During liquefaction, shake the sample three times; approximately every 20 minutes during the process.

After the liquefaction, samples are cooled to room temperature.

Use the "Dry-Grind Ethanol Calculator" to determine the appropriate amounts of glucoamylase, nutrient, antimicrobial, and yeast to achieve the necessary dry solids for each sample.

After addition of enzymes, set them to ferment at 30° C. in the growth chamber for 72 hours. A small hole should be punctured in each cap for ventilation during fermentation.

At 24, 48, and 72 hours, samples are prepared for ethanol analysis via GC.

Results and Discussion

24 Hours Data at 30%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 6.56 | 6.76 | 6.96 | 0.19 | 0.28 | 0.51 | 0.09 |
| Ethanol | Waxy | 10 | 6.71 | 6.87 | 7.03 | 0.15 | 0.22 | 0.40 | 0.07 |
| Ethanol | Diff | | −0.35 | −0.11 | 0.13 | 0.19 | 0.25 | 0.37 | 0.11 |

| Variable | Method | Variances | DF | t Value | Pr > |t| | Significance |
|---|---|---|---|---|---|---|
| Ethanol | Pooled | Equal | 18 | −0.99 | 0.34 | |
| Ethanol | Satterthwaite | Unequal | 17.1 | −0.99 | 0.34 | |

| Variable | Method | Num DF | Den DF | F Value | Pr > F | Significance |
|---|---|---|---|---|---|---|
| Ethanol | Folded F | 9 | 9 | 1.58 | 0.50 | |

24 Hours Data at 36%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 6.25 | 6.49 | 6.74 | 0.24 | 0.35 | 0.63 | 0.11 |
| Ethanol | Waxy | 10 | 6.59 | 6.82 | 7.06 | 0.23 | 0.33 | 0.60 | 0.10 |
| Ethanol | Diff | | −0.65 | −0.33 | −0.01 | 0.25 | 0.34 | 0.50 | 0.15 |

| Variable | Method | Variances | DF | t Value | Pr > \|t\| | Significance |
|---|---|---|---|---|---|---|
| Ethanol | Pooled | Equal | 18 | −2.2 | 0.042 | * |
| Ethanol | Satterthwaite | Unequal | 18 | −2.2 | 0.042 | |

| Variable | Method | Num DF | Den DF | F Value | Pr > F | Significance |
|---|---|---|---|---|---|---|
| Ethanol | Folded F | 9 | 9 | 1.1 | 0.88 | |

48 Hours Data at 30%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 8.11 | 8.60 | 9.09 | 0.47 | 0.69 | 1.26 | 0.22 |
| Ethanol | Waxy | 10 | 9.60 | 9.91 | 10.22 | 0.29 | 0.43 | 0.78 | 0.14 |
| Ethanol | Diff | | −1.85 | −1.31 | −0.77 | 0.43 | 0.57 | 0.85 | 0.26 |

| Variable | Method | Variances | DF | t Value | Pr > \|t\| | Significance |
|---|---|---|---|---|---|---|
| Ethanol | Pooled | Equal | 18 | −5.11 | <.0001 | ** |
| Ethanol | Satterthwaite | Unequal | 15 | −5.11 | 0.0001 | |

| Variable | Method | Num DF | Den DF | F Value | Pr > F | Significance |
|---|---|---|---|---|---|---|
| Ethanol | Folded F | 9 | 9 | 2.6 | 0.17 | |

48 Hours Data at 36%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 8.15 | 8.30 | 8.46 | 0.15 | 0.21 | 0.39 | 0.07 |
| Ethanol | Waxy | 10 | 9.53 | 9.92 | 10.32 | 0.38 | 0.55 | 1.00 | 0.17 |
| Ethanol | Diff | | −2.01 | −1.62 | −1.23 | 0.31 | 0.42 | 0.62 | 0.19 |

| Variable | Method | Variances | DF | t Value | Pr > \|t\| | Significance |
|---|---|---|---|---|---|---|
| Ethanol | Pooled | Equal | 18 | −8.7 | <.0001 | |
| Ethanol | Satterthwaite | Unequal | 11.7 | −8.7 | <.0001 | ** |

| Variable | Method | Num DF | Den DF | F Value | Pr > F | Significance |
|---|---|---|---|---|---|---|
| Ethanol | Folded F | 9 | 9 | 6.57 | 0.0098 | ** |

72 Hours Data at 30%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 9.67 | 10.20 | 10.74 | 0.51 | 0.74 | 1.36 | 0.24 |
| Ethanol | Waxy | 10 | 11.96 | 12.17 | 12.39 | 0.21 | 0.30 | 0.56 | 0.10 |
| Ethanol | Diff | | −2.50 | −1.97 | −1.44 | 0.43 | 0.57 | 0.84 | 0.25 |

| Variable | Method | Variances | DF | t Value | Pr > \|t\| | Significance |
|---|---|---|---|---|---|---|
| Ethanol | Pooled | Equal | 18 | −7.76 | <.0001 | |
| Ethanol | Satterthwaite | Unequal | 11.9 | −7.76 | <.0001 | ** |

-continued

| Variable | Method | Num DF | Den DF | F Value | Pr > F | Significance |
|---|---|---|---|---|---|---|
| Ethanol | Folded F | 9 | 9 | 5.97 | 0.014 | * |

72 Hours Data at 36%

| Variable | Line | N | Lower CL Mean | Mean | Upper CL Mean | Lower CL Std Dev | Std Dev | Upper CL Std Dev | Std Err |
|---|---|---|---|---|---|---|---|---|---|
| Ethanol | Nonwaxy | 10 | 10.02 | 10.36 | 10.70 | 0.32 | 0.47 | 0.86 | 0.15 |
| Ethanol | Waxy | 9 | 11.81 | 12.28 | 12.76 | 0.42 | 0.62 | 1.19 | 0.21 |
| Ethanol | Diff | | −2.45 | −1.92 | −1.39 | 0.41 | 0.55 | 0.82 | 0.25 |

| Variable | Method | Variances | DF | t Value | Pr > \|t\| | Significance |
|---|---|---|---|---|---|---|
| Ethanol | Pooled | Equal | 17 | −7.67 | <.0001 | ** |
| Ethanol | Satterthwaite | Unequal | 14.9 | −7.56 | <.0001 | |

| Variable | Method | Num DF | Den DF | F Value | Pr > F | Significance |
|---|---|---|---|---|---|---|
| Ethanol | Folded F | 8 | 9 | 1.74 | 0.43 | |

The types of NIL inbreds (waxy and non-waxy) were paired with two solids levels (30% and 36%) in a factorial design. Results from the factorial design examining the impact on fermentation in terms of ethanol yield support the hypothesis that the waxy NIL has a faster rate of ethanol accumulation and total ethanol yield in both solids levels. There was strong evidence of significant increased ethanol yield of the waxy NIL by time interaction with the exception of 24 hours at 30% solids. This may be due to variation inherent with fermentation process.

Randomization Schedule

| Solids | Variety | Order | Reps | Time Point |
|---|---|---|---|---|
| 36 | Control | 1 | 3 | 24, 48, 72 |
| 36 | Non-Waxy | 2 | 3 | 24, 48, 72 |
| 36 | Non-Waxy | 3 | 3 | 24, 48, 72 |
| 36 | Waxy | 4 | 3 | 24, 48, 72 |
| 36 | Non-Waxy | 5 | 3 | 24, 48, 72 |
| 36 | Waxy | 6 | 3 | 24, 48, 72 |
| 36 | Non-Waxy | 7 | 3 | 24, 48, 72 |
| 36 | Waxy | 8 | 3 | 24, 48, 72 |
| 36 | Waxy | 9 | 3 | 24, 48, 72 |
| 36 | Control | 10 | 3 | 24, 48, 72 |
| 36 | Non-Waxy | 11 | 3 | 24, 48, 72 |
| 36 | Waxy | 12 | 3 | 24, 48, 72 |
| 36 | Non-Waxy | 13 | 3 | 24, 48, 72 |
| 36 | Non-Waxy | 14 | 3 | 24, 48, 72 |
| 36 | Waxy | 15 | 3 | 24, 48, 72 |
| 36 | Non-Waxy | 16 | 3 | 24, 48, 72 |
| 36 | Waxy | 17 | 3 | 24, 48, 72 |
| 36 | Waxy | 18 | 3 | 24, 48, 72 |
| 36 | Control | 19 | 3 | 24, 48, 72 |
| 36 | Non-Waxy | 20 | 3 | 24, 48, 72 |
| 36 | Waxy | 21 | 3 | 24, 48, 72 |
| 36 | Non-Waxy | 22 | 3 | 24, 48, 72 |
| 36 | Waxy | 23 | 3 | 24, 48, 72 |
| 30 | Waxy | 1 | 3 | 24, 48, 72 |
| 30 | Non-Waxy | 2 | 3 | 24, 48, 72 |
| 30 | Non-Waxy | 3 | 3 | 24, 48, 72 |
| 30 | Non-Waxy | 4 | 3 | 24, 48, 72 |
| 30 | Control | 5 | 3 | 24, 48, 72 |
| 30 | Waxy | 6 | 3 | 24, 48, 72 |
| 30 | Non-Waxy | 7 | 3 | 24, 48, 72 |
| 30 | Non-Waxy | 8 | 3 | 24, 48, 72 |
| 30 | Non-Waxy | 9 | 3 | 24, 48, 72 |
| 30 | Non-Waxy | 10 | 3 | 24, 48, 72 |
| 30 | Waxy | 11 | 3 | 24, 48, 72 |
| 30 | Waxy | 12 | 3 | 24, 48, 72 |
| 30 | Non-Waxy | 13 | 3 | 24, 48, 72 |
| 30 | Control | 14 | 3 | 24, 48, 72 |
| 30 | Waxy | 15 | 3 | 24, 48, 72 |
| 30 | Waxy | 16 | 3 | 24, 48, 72 |
| 30 | Waxy | 17 | 3 | 24, 48, 72 |
| 30 | Waxy | 18 | 3 | 24, 48, 72 |
| 30 | Non-Waxy | 19 | 3 | 24, 48, 72 |
| 30 | Non-Waxy | 20 | 3 | 24, 48, 72 |
| 30 | Waxy | 21 | 3 | 24, 48, 72 |
| 30 | Waxy | 22 | 3 | 24, 48, 72 |
| 30 | Control | 23 | 3 | 24, 48, 72 |

Experiment 3

Headspace Analysis of a Fermented Sample

Research Objective: Determine if Headspace Gas Chromatography is a Viable Option for the Ethanol HTS Platform.
Research Hypothesis:

Headspace gas chromatography coupled with flame ionization detection has been identified in the literature as a common method used to determine blood alcohol content. This method of ethanol detection was applied to an alcoholic fermentation of maize in order to determine if the method was applicable for a high throughput screening platform. Included in the analysis were an ethanol sample, the analyte of interest, and an isopropanol sample, the intended internal standard for the proposed HTS method. The 2 alcohols were analyzed in order to determine if these could be resolved in a chromatogram.

Technical Approach:

An Hewlett-Packard HP6890GC system with a Hewlett-Packard HP7694 headspace autosampler and an FID was used to analyze 3 sample materials. The 3 sample materials were: A) a 15% aqueous ethanol standard, B) a 10% aqueous isopropanol standard and C) a fermented maize mash sample.

Work Plan:

Alcohol standards were created and dispensed in 20 ml headspace vials. The fermented maize mash was also placed in the 20 ml headspace vial. The samples were then analyzed following the same headspace and gas chromatography parameters.

Materials and Methods

Samples of fermented maize, a 15% aqueous ethanol standard and 10% isopropyl alcohol standard were prepared and placed in 20 ml headspace vials. The samples were then analyzed on the Hewlett-Packard headspace gas chromatograph with flame ionization detection. The column used in the GC was a DB1, (30 m×0.25 mm id, 0.25 μm film). The oven temperature was ramped from 55° to 100° C.

Results

The chromatogram of 15% ethanol standard shows good peak shape and a retention time of 2.01 minutes. There are no other peaks recorded on the chromatogram. The chromatogram of the fermented maize shows the ethanol peak at the same retention time as the standard, with a similar peak shape. There are a few minor peaks detected in the chromatogram, the largest of which is ≈0.25% of the height of the ethanol peak. The chromatogram of the 10% isopropanol standard shows a peak with a retention time of 3.26 minutes. The shape of the isopropanol peak is also good. The 3 sample chromatograms 15% Ethanol Standard, Fermented Maize and 10% Isopropanol Standard Discussion The use of headspace GC coupled with FID resulted in chromatograms that are very similar to those found in the literature. The analytical technique meets the requirements for the ethanol HTS platform. The resulting peak retention times and peak shapes of the ethanol and isopropanol samples indicate that resolving the 2 compounds will not be a problem.

Experiment 4

Investigation of NPA Volume and GC Method for High Throughput Fermentation Screening Research Objective Research Hypothesis:

Corn Ethanol Platform has developed a high throughput screening assay to measure the rate of ethanol accumulation and total ethanol yield using gas chromatography (GC) analysis. The current process uses 1% 1-propanol (NPA) as the internal standard and a single rinse method between the injections. The objectives of this study are to determine the volume at which the NPA should be added to the ferments to reduce measurement errors and determine which method (single or dual rinse) observes a reduction in errors between the front and back injectors.

Technical Approach:

144 fermentations will take place in 20 mL headspace vials. The 144 fermentations are divided into 4 treatments with 12 reps per time point. The time points are 24, 48, and 72 hours. The 4 treatments are: 1) Dual 1%; 2) Dual 2.5%; 3) Single 1%; and 4) Single 2.5%. Table below summarizes the treatment groups.

TABLE

Sample Matrix of Investigation of NPA Volume and GC Method for High Throughput Fermentation Screening

| GC Method | NPA Volume | Reps | Time Points |
|---|---|---|---|
| 1) Dual Rinse | 1% NPA | 36 (12 per time point) | 24, 48, 72 hours |
| 2) Single Rinse | 2.5% NPA | 36 (12 per time point) | 24, 48, 72 hours |
| 3) Dual Rinse | 2.5% NPA | 36 (12 per time point) | 24, 48, 72 hours |
| 4) Single Rinse | 1% NPA | 36 (12 per time point) | 24, 48, 72 hours |

Work Plan:

The samples will be fermented for 72 hours in the growth room at 30 C. At 24, 48, and 72 hours, samples will be analyzed for ethanol analysis via GC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Genencor ® Spezyme Xtra | Ethanol Tech ® AYF1177 Nutrient |
| Distilled water | Tetracycline |
| Shaker | Oven |
| 20 mL headspace vials and caps | Growth Chamber |
| Analytical Balance | Powder handling system |
| Liquid handling system | Liquid chromatography |

Moisture was measured on the corn flour using the Perten DA NIR7200.

Use the "Dry-Grind Ethanol Calculator" and the measured moisture determines the appropriate amounts of corn flour, water, and alpha amylase to achieve 30% dry solids for liquefaction and place into seventy two (72) 20 mL headspace vials.

Liquefactions were carried out in an oven at 85° C. for 90 minutes. During liquefaction, shake the sample three times; approximately every 20 minutes during the process.

After the liquefaction, samples were cooled to room temperature.

Use the "Dry-Grind Ethanol Calculator" to determine the appropriate amounts of glucoamylase, nutrient, antimicrobial, and yeast based on 30% liquefaction dry solids to add into each sample.

After addition of fermentation components, shake each vial very well, and then set them to ferment at 30° C. in the growth chamber for 72 hours. A small hole should be punctured in each cap for ventilation during fermentation.

Samples are taken at 24, 48, and 72 hours for ethanol analysis via GC. Refer to Table below for analysis.

TABLE

Sample Matrix of Investigation of NPA Volume and GC Method for High Throughput Fermentation Screening

| GC Method | NPA Volume | Reps | Time Points |
|---|---|---|---|
| 1) Dual Rinse | 1% NPA | 36 (12 per time point) | 24, 48, 72 hours |
| 2) Single Rinse | 2.5% NPA | 36 (12 per time point) | 24, 48, 72 hours |
| 3) Dual Rinse | 1% NPA | 36 (12 per time point) | 24, 48, 72 hours |
| 4) Single Rinse | 2.5% NPA | 36 (12 per time point) | 24, 48, 72 hours |

Results and Discussion
Ethanol data at 24 hours:

|  | Dual 2.5% | Dual 1% | Single 2.5% | Single 1% |
|---|---|---|---|---|
| Mean | 6.39 | 6.34 | 5.48 | 5.37 |
| St. Dev | 0.37 | 0.33 | 0.82 | 0.61 |
| % RSD | 5.77 | 5.17 | 14.96 | 11.37 |
| Range | 1.16 | 1.19 | 3.01 | 2.06 |
| SEM | 0.11 | 0.09 | 0.24 | 0.18 |

Ethanol data at 48 hours:

|  | Dual 2.5% | Dual 1% | Single 2.5% | Single 1% |
|---|---|---|---|---|
| Mean | 7.84 | 7.64 | 6.63 | 6.33 |
| St. Dev | 0.62 | 0.73 | 0.69 | 0.51 |
| % RSD | 7.97 | 9.61 | 10.36 | 7.98 |
| Range | 1.98 | 2.35 | 2.07 | 1.56 |
| SEM | 0.21 | 0.23 | 0.21 | 0.15 |

Ethanol data at 72 hours:

|  | Dual 2.5% | Dual 1% | Single 2.5% | Single 1% |
|---|---|---|---|---|
| Mean | 9.87 | 9.50 | 7.96 | 8.08 |
| St. Dev | 0.49 | 0.65 | 0.94 | 0.78 |
| % RSD | 5.00 | 6.84 | 11.79 | 9.60 |
| Range | 1.44 | 2.36 | 2.67 | 2.49 |
| SEM | 0.14 | 0.19 | 0.27 | 0.22 |

Representative sample of curves are in shown in FIG. 4a-h.

Experiment 6

Confirmation and Selection of Fermentation Components

Research Objective
Research Hypothesis:
One commercial available products screened have a measurable effect on the rate of ethanol accumulation or total ethanol yield when compared to our fermentation components. The leading components are Genencor's Spezyme Xtra alpha-amylase (commercial), Sigma's *A. Niger* glucoamylase (our benchmark), and Ethanol Tech's SLY yeast (benchmark). The nutrient and antibiotic components are still in question due to another competing component and sampling errors, respectively. The objective of this study is to ferment the leading and questionable components for confirmation of selection of fermentation components.

Technical Approach:
Nine (9) fermentations will take place in 50 ml conical tubes. The 9 fermentations will be divided into 3 treatment groups with 3 reps per treatment. Table below summarizes the treatment

TABLE

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | *A. Niger* GA | *A. Niger* GA | *A. Niger* GA |
| Nutrient | Urea | AYF1177 | AYF1177 |
| Antibiotic | Tetracycline | Tetracycline | Lactoside |
| Yeast | SLY yeast | SLY yeast | SLY yeast |

Work Plan:
The samples will be fermented for 72 hours in the growth room at 30 C. At 24, 48, and 72 hours, each sample will be sub-sampled and prepared for ethanol analysis via liquid chromatography.

Materials and Methods

| | |
|---|---|
| Yellow dent corn | Perten 3600 Disc Mill |
| Perten DA7200 | Urea 1 g/2 ml Stock |
| VWR incubator | Sigma *A. niger* Glucoamylase |
| 50 ml conical tubes | Analytical balance |
| Tetracycline (10 mg/ml in 50% EtOH stock solution). | Ethanol Tech AYF 1177 |
| Genencor Spezyme Xtra | Ethanol Tech SLY Yeast |
| Ethanol Tech Lactoside | Growth chamber |

Grind yellow dent corn using Perten 3600 Disc Mill, on setting 0.

Moisture is measured on the flour using Perten DA7200.

Use the "Enzyme Confirmation Calculator" and the measured moisture to determine the appropriate amounts of yellow dent corn flour, water, and alpha amylase (Genencor's Spezyme Xtra) to achieve 30% dry solids and place into nine (9) 50 ml conical tubes for liquefaction.

Liquefactions are carried out in an oven at 85° C. for 90 minutes. During liquefaction, shake or vortex each tube every 20 minutes.

After the liquefaction, cool samples down to room temperature, and then, the samples were divided according to their treatment groups: Treatment 1 (3 samples), Treatment 2 (3 samples), and Treatment 3 (3 samples). Refer to Table 1.

TABLE 1

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | *A. Niger* GA | *A. Niger* GA | *A. Niger* GA |
| Nutrient | Urea | AYF1177 | AYF1177 |
| Antibiotic | Tetracycline | Tetracycline | Lactoside |
| Yeast | SLY yeast | SLY yeast | SLY yeast |

Use the "Enzyme Confirmation Calculator" to determine the appropriate amounts of glucoamylase, nutrient, antibiotic, and yeast to add to each sample.

After following each treatment design, mix the tubes very well, and then set them to ferment at 30° C. for 72 hours. A small hole should be punctured in each cap for ventilation during fermentation.

Samples are taken at 24, 48, and 72 hours for ethanol analysis via liquid chromatography.

Results and Discussion

TABLE 1

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | A. Niger GA | A. Niger GA | A. Niger GA |
| Nutrient | Urea | AYF1177 | AYF1177 |
| Antibiotic | Tetracycline | Tetracycline | Lactoside |
| Yeast | SLY yeast | SLY yeast | SLY yeast |

Ethanol Data:

| | At 24 hours: | | | At 48 hours: | | | At 72 hours: | |
|---|---|---|---|---|---|---|---|---|
| | Rep | ETOH % | | Rep | ETOH % | | Rep | ETOH % |
| Treatment 1 | 1 | 4.57 | Treatment 1 | 1 | 6.99 | Treatment 1 | 1 | 9.23 |
| | 2 | 4.66 | | 2 | 7.3 | | 2 | 9.62 |
| | 3 | 4.65 | | 3 | 7.29 | | 3 | 10.11 |
| Treatment 2 | 1 | 5.88 | Treatment 2 | 1 | 9.39 | Treatment 2 | 1 | NA |
| | 2 | 8.02 | | 2 | 6.97 | | 2 | NA |
| | 3 | 8.72 | | 3 | 7.36 | | 3 | NA |
| Treatment 3 | 1 | 4.74 | Treatment 3 | 1 | 7.62 | Treatment 3 | 1 | 10.05 |
| | 2 | 4.81 | | 2 | 7.7 | | 2 | 10.37 |
| | 3 | 4.69 | | 3 | 7.23 | | 3 | 9.68 |

Statistical Analysis at 24 Time Point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 2.00 | 16.30 | 8.15 | 11.14 | 0.01 |
| Error | 6.00 | 4.39 | 0.73 | | |
| Corrected Total | | 8.00 | 20.70 | | |

| Source | DF | Type 1 SS | Mean Square | F Value | Pr > F |
|---|---|---|---|---|---|
| treatment | 2.00 | 16.30 | 8.15 | 11.14 | 0.01 |

| Source | DF | Type 3 SS | Mean Square | F Value | Pr > F |
|---|---|---|---|---|---|
| treatment | 2.00 | 16.30 | 8.15 | 11.14 | 0.01 |

| t Grouping | Mean | N | Treatment |
|---|---|---|---|
| A | 7.54 | 3.00 | 2 |
| B | 4.75 | 3.00 | 3 |
| B | 4.63 | 3.00 | 1 |

Statistical Analysis at 48 Hour Time Point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 2.00 | 0.77 | 0.38 | 0.64 | 0.56 |
| Error | 6.00 | 3.57 | 0.59 | | |
| Corrected Total | | 8.00 | 4.33 | | |

| Source | DF | Type 1 SS | Mean Square | F Value | Pr > F |
|---|---|---|---|---|---|
| treatment | 2.00 | 0.77 | 0.38 | 0.64 | 0.56 |

| Source | DF | Type 3 SS | Mean Square | F Value | Pr > F |
|---|---|---|---|---|---|
| treatment | 2.00 | 0.77 | 0.38 | 0.64 | 0.56 |

| t Grouping | Mean | N | Treatment |
|---|---|---|---|
| A | 7.91 | 3.00 | 2 |
| A | 7.52 | 3.00 | 3 |
| A | 7.19 | 3.00 | 1 |

Statistical Analysis at 72 Hour Time Point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 1.00 | 0.22 | 0.22 | 1.38 | 0.31 |
| Error | 4.00 | 0.63 | 0.16 | | |
| Corrected Total | | 5.00 | 0.84 | | |

| Source | DF | Type 1 SS | Mean Square | F Value | Pr > F |
|---|---|---|---|---|---|
| treatment | 1.00 | 0.22 | 0.22 | 1.38 | 0.31 |

| Source | DF | Type 3 SS | Mean Square | F Value | Pr > F |
|---|---|---|---|---|---|
| treatment | 1.00 | 0.22 | 0.22 | 1.38 | 0.31 |

| t Grouping | Mean | N | Treatment |
|---|---|---|---|
| A | 10.03 | 3.00 | 3 |
| A | 9.65 | 3.00 | 1 |

The nutrient/antibiotic combination of AYF1177/Tetracycline used in Treatment 2 was found to be significantly different from the Urea/Tetracycline and AYF1177/Lactoside treatment's mean ethanol yields at 24 hours. There were no significant differences observed at the 48 and 72 hour time points. The 72 hour fermentation data for Treatment 2 is unavailable. The substitution of AYF1177 for Urea in our benchmark resulted in a significant increase in mean ethanol yields in 24 and 48 hour ferments. As a result of the observations made in these 2 studies, AYF1177 and Tetracycline are used as the nutrient and antibiotic in the high throughput fermentation platform.

Based on the standard deviation values and % RSD values of each treatment, the dual GC method appears to have less variation between the injectors than the single GC method.

The 2.5% NPA, with lower intercepts and consistent slopes in the calibration curves, appears to have a better correlation than the 1% NPA. Based on the results presented here, the dual GC method with 2.5% NPA was selected to optimize the high throughput fermentation platform.

Experiment 7

Method Optimization of Raw Starch Fermentation

Research Objective
Research Hypothesis:
Corn Ethanol Platform has developed a high throughput screening assay to measure the rate of ethanol accumulation and total ethanol yield. In efforts to optimize the raw starch fermentation for calibration development, the objectives of this study are to: 1) determine the optimal doses of glucoamylase and yeast, 2) determine whether the pH of the ferments are within the desirable range, and 3) validate the pasteurization process used in the dry grind fermentation to inhibit yeast growth in the procedure.

Technical Approach:
Three hundred sixty (360) fermentations will take place in 20 mL headspace vials. The 360 fermentations are divided into 25 unique enzyme dose combinations of glucoamylase and yeast at 33% solids. Each enzyme dose combination will be compared to current dose rates of glucoamylase and yeast at 33% solids (100-100%=benchmark treatment). Each enzyme dose combination will have 4 reps per time point. The time points are 24, 48, and 72 hours. Table 1 summarizes the treatment groups.

An additional 5 treatments of the 100-100% benchmark dose combination will be prepared to investigate what effect the pasteurization process utilized on the high throughput fermentation screening platform has on the ethanol generation of the raw starch fermentation process. Three treatments of the 100-100% dose combination without pasteurization will be compared to 3 treatments which are pasteurized.

An additional 25 fermentations will take place in 20 mL headspace vials for pH measurements only. The measurements will occur before and after the addition of tetracycline, glucoamylase, and yeast and after 72 hours of fermentation. Each enzyme dose combination will have 1 rep.

TABLE

Sample Matrix for Method Optimization of Raw Starch Fermentation

| | Sample | Time Point | Reps | Pasteurization |
|---|---|---|---|---|
| 1 | 75-75 | 24, 48, 72 | 12 (4/time point) | Yes |
| 2 | 75-88 | 24, 48, 72 | 12 (4/time point) | Yes |
| 3 | 75-100 | 24, 48, 72 | 12 (4/time point) | Yes |
| 4 | 75-112 | 24, 48, 72 | 12 (4/time point) | Yes |
| 5 | 75-125 | 24, 48, 72 | 12 (4/time point) | Yes |
| 6 | 88-75 | 24, 48, 72 | 12 (4/time point) | Yes |
| 7 | 88-88 | 24, 48, 72 | 12 (4/time point) | Yes |
| 8 | 88-100 | 24, 48, 72 | 12 (4/time point) | Yes |
| 9 | 88-112 | 24, 48, 72 | 12 (4/time point) | Yes |
| 10 | 88-125 | 24, 48, 72 | 12 (4/time point) | Yes |
| 11 | 100-75 | 24, 48, 72 | 12 (4/time point) | Yes |
| 12 | 100-88 | 24, 48, 72 | 12 (4/time point) | Yes |
| 13 | 100-100 | 24, 48, 72 | 12 (4/time point) | Yes |
| 14 | 100-100 | 24, 48, 72 | 12 (4/time point) | Yes |
| 15 | 100-100 | 24, 48, 72 | 12 (4/time point) | Yes |
| 16 | 100-100 | 24, 48, 72 | 12 (4/time point) | NO |
| 17 | 100-100 | 24, 48, 72 | 12 (4/time point) | NO |
| 18 | 100-100 | 24, 48, 72 | 12 (4/time point) | NO |
| 19 | 100-112 | 24, 48, 72 | 12 (4/time point) | Yes |
| 20 | 100-125 | 24, 48, 72 | 12 (4/time point) | Yes |
| 21 | 112-75 | 24, 48, 72 | 12 (4/time point) | Yes |
| 22 | 112-88 | 24, 48, 72 | 12 (4/time point) | Yes |
| 23 | 112-100 | 24, 48, 72 | 12 (4/time point) | Yes |
| 24 | 112-112 | 24, 48, 72 | 12 (4/time point) | Yes |
| 25 | 112-125 | 24, 48, 72 | 12 (4/time point) | Yes |
| 26 | 125-75 | 24, 48, 72 | 12 (4/time point) | Yes |
| 27 | 125-88 | 24, 48, 72 | 12 (4/time point) | Yes |
| 28 | 125-100 | 24, 48, 72 | 12 (4/time point) | Yes |
| 29 | 125-112 | 24, 48, 72 | 12 (4/time point) | Yes |
| 30 | 125-125 | 24, 48, 72 | 12 (4/time point) | Yes |
| | | TOTAL | 360 | |

Work Plan:
The samples will randomized over 2 days of fermentation. Each sample will be fermented for 72 hours in the growth room at 30C. At 24, 48, and 72 hours, each sample will be sub-sampled and prepared for ethanol analysis via HPLC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Distilled water | Tetracycline 10 mg/ml in 50% EtOH |
| Fluid Management ® 5G High Speed Shaker | 0.9M Sulfuric Acid |
| 20 mL headspace vials and caps | Growth Chamber |
| Analytical Balance | SDSI 2300 Powder Dispensing System |
| Hamilton MicroLab ® 500 Liquid Handling System | Agilent 1200 series HPLC with RID & Quaternary Pump System |
| pH indicator strips | 22 Gauge Needles |

Measure the moisture of the corn flour using the Perten DA NIR7200.

Use the "Raw Starch Calculator" and the measured moisture to determine the appropriate amounts of corn flour, water, sulfuric acid, tetracycline, glucoamylase, and yeast to achieve 33% solids and place into three hundred sixty (360) 20 mL headspace vials.

Add the components in the following order: water, sulfuric acid, tetracycline, glucoamylase, and yeast.

Vortex the vials after the addition of water, and vortex the vials a second time after the addition of sulfuric acid. Refer to Table 1.

After the addition of tetracycline, glucoamylase, and yeast, use the high speed shaker to mix the fermentation components very well, and then set them to ferment at 30° C. in the growth chamber for 72 hours. A needle should be punctured in each cap for ventilation during fermentation.

Samples are taken at 24, 48, and 72 hours for ethanol analysis via HPLC.

Results and Discussion
Objective 1—GA & Yeast Doses Investigated
The data analysis of the glucoamylase and yeast dosage study was performed.

An analysis of variance was performed controlling for session, glucoamylase dose, yeast dose, and the interaction between glucoamylase and yeast. Separate analyses were performed for each time point.

At 24 hours, there was evidence of differences in ethanol concentration attributable to dose of glucoamylase ($p=0.021$), but there was not evidence of differences attributable to dose of yeast ($p=0.840$) or to an interaction effect ($p=0.973$). Least squares means were computed for each dose of glucoamylase, but there was not sufficient evidence to suggest that any experimental dose of glucoamylase resulted in higher ethanol concentrations than was observed with the baseline dose. See Table 1 at the end of the report.

At 48 hours, there was strong evidence of differences in ethanol concentration attributable to dose of glucoamylase ($p<0.001$), but there was not evidence of differences attributable to dose of yeast ($p=0.748$) or to an interaction effect ($p=0.914$). Least squares means were computed for each dose of glucoamylase. There was weak evidence to suggest that the 112.5% and 125% doses of glucoamylase resulted in higher ethanol concentration than did the 100% dose of glucoamylase. However, the relative magnitude of the increase in ethanol concentrations is less than 2% and likely is not of practical significance. See Table 1 at the end of the report.

At 72 hours, there was no evidence of differences in ethanol concentration attributable to dose of glucoamylase ($p=0.419$), dose of yeast ($p=0.193$) or to an interaction effect ($p=0.360$). Least squares means are presented in Table 1 at the end of this report.

Results from a factorial design examining the impact of manipulating the dose of glucoamylase and the dose of yeast do not support the hypothesis that the dose of yeast affects ethanol concentration, at least within the range of doses included in the study (75%-125% of baseline). There was weak evidence of an increased ethanol concentration with higher levels of glucoamylase at 48 hours only, but the magnitude of this effect is less than 2% in size and likely is not of practical significance.

TABLE

Least Squares Means for Ethanol Concentration by Time and Dose of GA

| Glucoamylase Dose | Ethanol Concentration at: | | |
|---|---|---|---|
| | 24 Hours | 48 Hours | 72 Hours |
| 75.0% | 8.85 | 14.36 | 17.27 |
| 87.5% | 9.35 | 14.83 | 17.48 |
| 100.0% | 9.71 | 14.83 | 17.68 |
| 112.5% | 9.53 | 15.08 | 17.79 |
| 125.0% | 9.82 | 15.09 | 17.00 |

Plots of this data can be generated. Plots of the least squares means for ethanol content vs. glucoamylase concentration, illustrating the differences observed between the glucoamylase treatments at the 24, 48 and 72 hour fermentation periods can be visualized.

Objective 2—pH Measurements

The raw starch fermentation method calls for the use of 0.9 M sulfuric acid at a rate of 0.0175 ml/g of dry flour to adjust the pH to 4.2 before fermentation begins. We found that gave us a pH of 4.9 before and after the addition of tetracycline, glucoamylase, and yeast. After 72 hours of fermentation, the pH dropped to 4.2. Table below summarizes the results of the pH measurements.

TABLE

Resulting pH values after addition of $H_2SO_4$, Yeast and after 72 hr Fermentation

| Sample | | pH Reading After $H_2SO_4$ Addition | pH Reading After Yeast Addition | pH Reading After 72 Hours Fermentation |
|---|---|---|---|---|
| 1 | 75-75 | 4.6 | 4.9 | 4.2 |
| 2 | 75-88 | 4.6 | 4.9 | 4.2 |
| 3 | 75-100 | 4.9 | 4.9 | 4.2 |
| 4 | 75-112 | 4.6 | 4.9 | 4.2 |
| 5 | 75-125 | 4.9 | 4.9 | 4.2 |
| 6 | 88-75 | 4.9 | 4.9 | 4.2 |
| 7 | 88-88 | 4.6 | 4.9 | 4.2 |
| 8 | 88-100 | 4.6 | 4.9 | 4.2 |
| 9 | 88-112 | 4.9 | 4.9 | 4.2 |
| 10 | 88-125 | 4.6 | 4.9 | 4.2 |
| 11 | 100-75 | 4.9 | 4.9 | 4.2 |
| 12 | 100-88 | 4.9 | 4.9 | 4.2 |
| 13 | 100-100 | 4.9 | 4.9 | 4.2 |
| 14 | 100-112 | 4.9 | 4.9 | 4.2 |
| 15 | 100-125 | 4.9 | 4.9 | 4.2 |
| 16 | 112-75 | 5.2 | 5.2 | 4.4 |
| 17 | 112-88 | 5.2 | 5.2 | 4.4 |
| 18 | 112-100 | 5.2 | 5.2 | 4.4 |
| 19 | 112-112 | 5.2 | 4.9 | 4.2 |
| 20 | 112-125 | 5.2 | 4.9 | 4.2 |
| 21 | 125-75 | 4.9 | 4.9 | 4.4 |
| 22 | 125-88 | 4.9 | 4.9 | 4.4 |
| 23 | 125-100 | 4.9 | 4.9 | 4.2 |
| 24 | 125-112 | 4.9 | 4.9 | 4.2 |
| 25 | 125-125 | 4.9 | 4.9 | 4.2 |

Objective 3—Arresting Method

Significant differences were observed between the treatments that were pasteurized and the treatments that were not pasteurized. The untreated samples continued to increase in ethanol over time and are significantly greater than the dose combinations that were treated with 45 minute pasteurization, indicating that yeast growth has been arrested in the pasteurized samples. Table below summarizes the mean ethanol percent at each time period and the treatment significance between the pasteurized and untreated samples.

TABLE

Treatment Significance and Mean Ethanol Percent at Each Time Period

| | With Pasteurization | Without Pasteurization | P-Values |
|---|---|---|---|
| 24 Hours | 9.48 | 10.81 | 0.0003 |
| 48 Hours | 14.93 | 16.82 | <.0001 |
| 72 Hours | 17.63 | 18.91 | <.0001 |

Experiment 8

Seed Selection based on Ethanol

The method of selecting seed for use in a monocot or dicot breeding and/or development program. This high throughput screen is very useful for selecting grass seeds with increased ethanol content for use in breeding or for commercial use of the seed. For example, grass seeds such as sorghum, wheat, oats, switch grass, or maize may be selected with this high throughput screen directly.

This screening method destroys the analyzed seed so there must be around 500-1000 seeds in total allow for screening with some seeds being retained for use as selected seeds for breeding. Alternatively, use of the NIR seed calibration, developed by the use of the screen to detect high ethanol content within maize seeds can be employed in a non-seed destruct method. This calibration allows even the very early breeding material (when there are few seeds) to be analyzed for ethanol content and then based on the analysis either selected for or discarded from use in further breeding.

A NIR calibration or results from the screen can be used to select inbred seeds or hybrid seeds for high, meduim or low ethanol content. Either the calibration or the screen result will allow the breeder or hybrid developer to select inbreds for: breeding, development or use in hybrid combinations based on ethanol content. Additionally, the NIR calibration or screen results can be used to select hybrids which will produce high levels of ethanol content from the grain. Additionally, grain harvested from hybrid plants can be analyzed by either method to select hybrid seed which produces the highest level of ethanol from the grain. This selected material can be used in a breeding program that continually reassesses each generation for ethanol or it can be used intermittently within the breeding process or just as a final selection tool.

Because NIR calibrations and screen results are possible on subsets of seeds components, the starch itself or just a portion of the seed, for example an embryo less seed, very small quantities of breeding seeds can be analyzed according to the present invention for ethanol content. If embryo less seeds are used then the embryos of these seeds can be employed in embryo rescue techniques to still produce a plant. Thus when the invention employs a step of embryo removal from the seed both the NIR ethanol calibration and the screen are non seed destruct processes. Non seed destruct is important when seeds are limited in number such as seeds from a segregating breeding population, doubled haploid seeds or seeds from lines that are not fully fixed.

Additionally, because the screen allows for testing of different fermentation cocktails the present invention allows different types of seed to be selected for use in hybrids that are processed through ethanol plants that employ different fermentation cocktails. This screen also allows hybrid blends to be selected and developed so that hybrid seed with produce grain that provides the highest ethanol content can be produced in regardless of which fermentation cocktails ethanol processors are employing. Hybrid blends are very useful in an area where there may be more than one ethanol processing plant and these different plants are using different enzymes, or different levels of enzymes during the ethanol production.

DEFINITIONS

Definitions for Calculations

Dry Grind Calculator

Liquefaction
  Given variables (as an example):
    ul's of benchmark amylase/dry gram corn flour=0.29
    Commodity corn % moisture=5% (measured by Perten Diode Array 7200 instrument)
    Wet commodity corn to weigh into each vial (g wet weight)=3 g
    Target % dry solids liquefaction=30%
  Dry gram corn flour for liquefaction (g dry weight):

Wet commodity corn (g wet weight)−((Wet commodity corn (g wet weight)×(Commodity Corn % moisture/100))

$3-(3\times(5/100))=2.85$ g

Total ul's of benchmark amylase to add to each vial at $1/25$ dilution:

Dry gram corn flour for liquefaction (g dry weight)×(ul's of benchmark amylase/dry gram corn flour)×25

$3-2.85\times0.29\times25=20.66$ ul

Water in corn (g weight):

Wet commodity corn (g wet weight)−Dry gram corn flour for liquefaction (g dry weight)

$3-2.85=0.15$ g

Total water volume in each vial (ml):

(Dry gram corn flour for liquefaction (g dry weight)/30%)−Dry gram corn flour for liquefaction (g dry weight)−Water in corn (g weight)

$(2.85/30\%)-2.85-0.15=6.50$ ml

Water to add to each vial (ml):

Total water volume in each vial (ml)−((Total ul's of benchmark to add to each vial at $1/25$ dilution/1000)+Water in corn (g weight))

$6.50-((20.66/1000)+0.15)=6.33$ ml

Total mass of liquefact (g):

Wet commodity corn (g wet weight)+Total water volume in each vial (ml)

$3+6.50=9.50$ g

Fermentation
  Given variables (as an example):
    Tetracycline 10 mg/ml use rate per gram flour (ml/g flour)=0.005 AYF1177 use rate per gram flour (ml/g flour)=0.00015
    A. niger glucoamylase use rate per gram flour (ul/g flour)=0.963
    SLY yeast use rate per gram flour (ul/g slurry)=10
  Desired mass of corn flour in ferment (g dry weight):
  Dry gram corn flour for liquefaction (g dry weight)
  2.85 g
  Mass of liquefact needed for ferment (g):

((Wet commodity corn (g wet weight)+Total water volume in each vial (ml))/Dry gram corn flour for liquefaction (g dry weight))×Desired mass of corn flour in ferment (g dry weight)

$((3+6.50)/2.85)\times2.85=9.50$ g

Tetracycline 10 mg/ml in 50% EtOH stock solution to add to each vial (ml):

Desired mass of corn flour in ferment (g dry weight)× Tetracycline 10 mg/ml use rate (ml/g flour)

$2.85\times0.005=0.01425$ ml

AYF1177 at $1/20$ dilution to add to each vial (ml):

Desired mass of corn flour in ferment (g dry weight)× AYF1177 use rate (ml/g flour)×

$2.85\times0.00015\times20=0.00855$ ml

A. niger glucoamylase at $1/20$ dilution to add to each vial (ml):

(Desired mass of corn flour in ferment (g dry weight)× A. niger glucoamylase use rate (ul/g flour)×20)/1000

$(2.85\times0.963\times20)/1000=0.0549$ ml

SLY yeast at $\frac{1}{10}$ dilution to add to each vial (ml):

(Total mass of liquefact (g)×SLY yeast use rate (ul/g flour)×10)/1000

(9.50×10×10)/1000=0.95 ml

Sum volume of liquids to be added to ferment (ml):

Tetracycline 10 mg/ml in 50% EtOH stock solution (ml)+*AYF*1177 at $\frac{1}{20}$ dilution (ml)+*A. niger* glucoamylase at $\frac{1}{20}$ dilution (ml)+*SLY* yeast at I/O dilution (ml)

0.01425+0.00855+0.0549+0.95=1.03 ml

% Dry solids for fermentation:

Desired mass of corn flour in ferment (g dry weight)/ (Mass of liquefact needed for ferment (g)+Sum volume of liquids to be added to ferment (ml))

(2.85/(9.50+1.03))×100=27.07%

Raw Starch Calculator

Liquefaction
NA
Fermentation
  Given variables (as an example):
    Corn flour moisture content %=5% (measured by Perten Diode Array 7200 instrument)
    Wet commodity corn to weigh into each vial (g wet weight)=3 g
    Target % dry solids=33%
    0.9M H2SO4 use rate per gram flour (ml/g flour)= 0.0175
    Tetracycline 10 mg/ml use rate per gram flour (ml/g flour)=0.005
    *A. niger* glucoamylase use rate per gram flour (ml/g flour)=0.00521
    SLY yeast use rate per gram flour (ml/g flour)=0.03
  Dry gram corn flour for fermentation reaction (g dry weight):

Wet commodity corn (g wet weight)−((Wet commodity corn (g wet weight)×(Corn flour moisture content %/100))

3−(3×($\frac{5}{100}$))=2.85 g

Water in corn (g weight):

Wet commodity corn (g wet weight)−Dry gram corn flour for fermentation reaction (g dry weight)

3−2.85=0.15 g

Total water volume in each vial (ml):

(Dry gram corn flour for fermentation reaction (g dry weight)/33%)−Dry gram corn flour for fermentation reaction (g dry weight)−Water in corn (g weight)

(2.85/33%)−2.85−0.15=5.64 ml

Water to add to each vial (ml):

Total water volume in each vial (ml)−(0.9M H2SO4 (ml)+Tetracycline at 10 mg/ml (ml)+*A. niger* glucoamylase at $\frac{1}{10}$ dilution (ml)+SLY yeast at $\frac{1}{10}$ dilution (ml))

5.64−(0.05+0.0143+0.148+0.855)=4.57 ml 0.9M H2SO4 to add to each vial (ml):

Dry gram corn flour for fermentation reaction (g dry weight)×0.9M H2SO4 use rate (ml/g flour)

2.85×0.0175=0.05 ml

Tetracycline 10 mg/ml in 50% EtOH stock solution to add to each vial (ml):

Dry gram corn flour for fermentation reaction (g dry weight)×Tetracycline use rate (ml/g flour)

2.85×0.005=0.0143 ml

*A. niger* glucoamylase at $\frac{1}{10}$ dilution to add to each vial (ml):

Dry gram corn flour for fermentation reaction (g dry weight)×*A. niger* glucoamylase use rate (ml/g flour)×10

2.85×0.00521×10=0.148 ml

SLY yeast at $\frac{1}{10}$ dilution to add to each vial (ml):

Dry gram corn flour for fermentation reaction (g dry weight)×SLY yeast use rate (ml/g flour)×10

2.85×0.03×10=0.855 ml

Fermentation reaction sum (ml):

Tetracycline 10 mg/ml (ml)+*A. niger* glucoamylase $\frac{1}{10}$ dilution (ml)+SLY yeast $\frac{1}{10}$ dilution (ml)

0.0143+0.148+0.855=1.02 ml

Experiment 8

Seed Selection Based on Ethanol

The method of selecting seed for use in a monocot or dicot breeding and/or development program. This high throughput screen is very useful for selecting grass seeds with increased ethanol content for use in breeding or for commercial use of the seed. For example, grass seeds such as sorghum, wheat, oats, switch grass, or maize may be selected with this high throughput screen directly.

This screening method destroys the analyzed seed so there must be around 500-1000 seeds in total allow for screening with some seeds being retained for use as selected seeds for breeding. Alternatively, use of the NIR seed calibration, developed by the use of the screen to detect high ethanol content within maize seeds can be employed in a non-seed destruct method. This calibration allows even the very early breeding material (when there are few seeds) to be analyzed for ethanol content and then based on the analysis either selected for or discarded from use in further breeding.

A NIR calibration or results from the screen can be used to select inbred seeds or hybrid seeds for high, medium or low ethanol content. Either the calibration or the screen result will allow the breeder or hybrid developer to select inbreds for: breeding, development or use in hybrid combinations based on ethanol content. Additionally, the NIR calibration or screen results can be used to select hybrids which will produce high levels of ethanol content from the grain. Additionally, grain harvested from hybrid plants can be analyzed by either method to select hybrid seed which produces the highest level of ethanol from the grain. This selected material can be used in a breeding program that continually reassesses each generation for ethanol or it can be used intermittently within the breeding process or just as a final selection tool.

Because NIR calibrations and screen results are possible on subsets of seeds components, the starch itself or just a portion of the seed, for example an embryo less seed, very small quantities of breeding seeds can be analyzed according to the present invention for ethanol content. If embryo less seeds are used then the embryos of these seeds can be employed in embryo rescue techniques to still produce a plant. Thus when the invention employs a step of embryo removal from the seed both the NIR ethanol calibration and the screen are non seed destruct processes. Non seed destruct is important when seeds are limited in number such as seeds from a segregating breeding population, doubled haploid seeds or seeds from lines that are not fully fixed.

Additionally, because the screen allows for testing of different fermentation cocktails the present invention allows different types of seed to be selected for use in hybrids that are processed through ethanol plants that employ different fermentation cocktails. This screen also allows hybrid blends to be selected and developed so that hybrid seed with produce grain that provides the highest ethanol content can be produced in regardless of which fermentation cocktails ethanol processors are employing. Hybrid blends are very useful in an area where there may be more than one ethanol processing plant and these different plants are using different enzymes, or different levels of enzymes during the ethanol production.

The present invention provides a method for selection of seed of large or small quantities, segregating or unsegregating seed which will when fermented have a high ethanol content; through employing a NIR calibration developed by the high through put screen or the screening that allows seed to be selected for further use.

The High Throughput Screening Platform is made up of a number of processes and allows for the development of a seed calibration. These include a. grinding, b. drying corn flour, c. weighing flour, d. water, nutrient, antibiotic and enzyme addition, e. liquefaction, add fermentation cocktail, f. fermentation, stop fermentation, g. pasteurization, and h. headspace analysis via gas chromatography. The calculator for different components is based on g of dry flour and all liquefactions and fermentations are assembled accordingly. Therefore it is imperative that the percent moisture of corn flour be determined.

i) Grinding—standard disc mill grinder is used.
j) Drying corn flour—the corn flour is driven to a terminal moisture level in a desiccating cabinet. The RH of the moisture cabinet may be from 5 to 20%, with a temperature range of 20 to 35° C.
k) Weighing Flour—Corn flour is weighed in a moisture-controlled glove box using an automated flour-dispensing unit. The RH of the glove box is maintained from 0-20%.
l) Addition of water, nutrient, antibiotic and enzymes— Each of the components listed are dispensed using computer controlled, repeating, dispensing units. Dispensing ranges are from 10 ul to 10 ml
m) Liquefaction—performed at a temperature range of about 75 to 95° C. for about 1 to 2 hours.
n) Fermentation—performed in 30±5° C. growth chambers. Ferments are allowed to grow for 24, 48 and 72 hours.
o) Pasteurization—to stop the fermentation process, the samples are pasteurized in a convected oven set at 80-90° C. for a period of 40-60 minutes.
p) Headspace analysis via gas chromatography—to analyze the samples ethanol content headspace GC analysis is utilized. The sample is incubated at 45±5° C. for 1.5 to 1.8 minutes. A headspace sample is then removed with a 46±5° C. heated syringe. The syringe then is injected into a 250±5° C. injection port, with a split flow of 25:1. The sample components are separated on an Agilent DB-ALC1 column at an isothermic oven temperature of 75±5° C. with a column flow of 7.5±0.5 ml/min.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system used to calibrate for a near infrared analytical testing device configured to screen for ethanol production yield of an ethanol-producing material, the system comprising:
   a first analytical testing device configured to interact with a sample material and collect a first signal associated with a characteristic parameter of the sample material, the characteristic parameter being capable of enabling evaluation of ethanol production yield for plant material corresponding substantially in composition to the sample material;
   a drying unit in communication with the first analytical testing device, the drying unit being configured to drive the sample material to a substantially standard moisture level, so as to form a dried sample material, the first analytical testing device being configured to interact with the dried sample material and collect a second signal associated with the characteristic parameter;
   a fermentation unit in communication with at least one of the drying unit and the first analytical testing device, the fermentation unit being configured to ferment the dried sample material, so as to form a fermented sample material; and
   a second analytical testing device in communication with the fermentation unit, the second analytical testing device being configured to interact with the fermented sample material and collect a reference measurement associated with the characteristic parameter, the reference measurement being capable of correlation to at least one of the first and second signals for building a calibration model used to evaluate ethanol production yield of plant material corresponding substantially in composition to the sample material.

2. A system according to claim 1 further comprising a preparation unit in communication with the first analytical testing device, the preparation unit being configured to prepare a seed sample material so as to form the sample material for interaction with the first analytical device.

3. A system according to claim 1 wherein the sample material is driven to a substantially standard moisture level of between about 5% and 8%.

4. A system according to claim 1 wherein the fermentation unit is configured to receive a vial container adapted to carry the dried sample material therein, the vial container being adapted to provide a predetermined headspace for performing fermentation of the dried sample material.

5. A system according to claim 4 wherein the predetermined headspace is about 20 milliliters.

6. A system according to claim 1 wherein the first analytical testing device comprises a near infrared testing device and the second analytical testing device comprises a gas chromatography testing device.

7. A system according to claim 1 further comprising a third analytical testing device in communication with the second analytical testing device, the third analytical testing device being configured to provide a supplemental reference measurement associated with the characteristic parameter, the supplemental reference measurement being capable of correlation to at least one of the first signal, the second signal, and the reference measurement for building the calibration model.

8. A system according to claim 7 wherein one of the second and third analytical testing devices is configured to implement gas chromatography and the other of the second and third analytical testing devices is configured to implement high performance liquid chromatography.

9. A system according to claim 1 wherein the sample material is dried to a terminal moisture level.

10. A system according to claim 1 wherein the characteristic parameter comprises a fermentation property of the sample material.

11. A system according to claim 1 wherein the sample material comprises an agricultural seed material.

12. A system according to claim 1 wherein the first analytical testing device is configured to probe the sample material and collect near infrared electromagnetic radiation.

13. A method employing the system according to claim 1 for determining a fermentation characteristic parameter of an agricultural seed material, the method comprising:
preparing the agricultural seed material to form a powder sample;
drying the powder sample to a substantially standard moisture level;
fermenting the powder sample to form a fermented sample; and
analyzing the fermented sample for a fermentation property.

14. A method employing the system according to claim 1 for determining a fermentation characteristic parameter of a starch material, the method comprising:
preparing a starch material;
drying the starch material to a substantially standard moisture level;
fermenting the starch material; and
analyzing the starch material for a fermentation property.

15. A method employing the system according to claim 1 for determining an enzyme characteristic parameter during fermentation of an agricultural seed material, the method comprising:
drying a ground seed sample or a portion of a ground seed sample to a substantially standard moisture level;
fermenting the seed sample; and
analyzing the seed sample for an enzyme property.

16. A system testing device configured according to claim 1 to screen for ethanol production yield of an ethanol-producing material, the system comprising:
a sample preparation unit forming sample material;
a drying unit adapt to accept prepared sample material, the drying unit being configured to drive the sample material to a substantially standard moisture level, so as to form a dried sample material;
a fermentation unit adapted to accept the dried sample material from at least one of the drying unit, the fermentation unit being configured to ferment the dried sample material, so as to form a fermented sample material; and
a gas chromatography testing device adapted to accept fermented sample material from the fermentation unit, the device provides a reference measurement associated with the fermented sample material with a gas chromatography testing device to evaluate ethanol production yield of plant material corresponding substantially in composition to the sample material.

17. A method of calibrating for a near infrared analytical testing device configured to screen for ethanol production yield of an ethanol-producing material, the method comprising:
collecting a first signal associated with a sample material with a first analytical testing device, the first signal being associated with a characteristic parameter of the sample material, the characteristic parameter being capable of enabling evaluation of ethanol production yield for plant material corresponding substantially in composition to the sample material;
drying the sample material to a substantially standard moisture level;
collecting a second signal associated with a sample material with the first analytical testing device, the second signal being associated with the characteristic parameter;
fermenting the sample material;
collecting a reference measurement associated with the sample material with a second analytical testing device, the reference measurement being associated with the characteristic parameter of the sample material; and
correlating the reference measurement to at least one of the first and second signals to build a calibration model used for evaluating ethanol production yield of plant material corresponding substantially in composition to the sample material.

18. A method according to claim 17 further comprising grinding the sample material for interaction with the first analytical device.

19. A method according to claim 17 wherein drying the sample material to a substantially standard moisture level further comprises driving the sample material to a substantially standard moisture level of between about 5% and 8%.

20. A method according to claim 17 wherein fermenting the sample material further comprises fermenting the sample material received in a vial container configured to carry the sample material therein, the vial container being further configured to provide a predetermined headspace for performing fermentation of the sample material.

21. A method according to claim 20 wherein the predetermined headspace is about 20 milliliters.

22. A method according to claim 17 wherein collecting a first and second signal further comprises collecting a first and second signal with a first analytical testing device comprising a near infrared spectrometer device, and collecting a reference measurement further comprises collecting a reference measurement with a second analytical testing device implementing gas chromatography.

23. A method according to claim 17 further comprising:
  collecting a supplemental reference measurement with a third analytical testing device, the supplemental reference measurement being associated with the characteristic parameter; and
  correlating the supplemental reference measurement to at least one of the first signal, the second signal, and the reference measurement for building the calibration model.

24. A method according to claim 23 wherein collecting a reference measurement further comprises collecting a reference measurement with a second analytical testing device configured to implement one of gas chromatography and high performance liquid chromatography, and collecting a supplemental reference measurement further comprises collecting a supplemental reference measurement with a third analytical testing device configured to implement the other of gas chromatography and high performance liquid chromatography.

25. A method according to claim 17 wherein collecting a first signal further comprises collecting a first signal associated with a sample material comprising an agricultural seed material.

26. A method according to claim 17 wherein collecting a first signal further comprises collecting a first signal associated with a characteristic parameter comprising a fermentation property of the sample material.

27. A method according to claim 17 further comprising probing the sample material with the first analytical testing device comprising a near infrared spectrometer device such that near infrared electromagnetic radiation is capable of being detected.

28. A method according to claim 17 wherein fermenting the sample material further comprises selecting a fermentation mixture, and adding the fermentation mixture to the sample material.

29. A method according to claim 28 wherein the fermentation mixture is selected from a combination of:
  water;
  nutrient;
  antibiotic; and
  enzyme.

30. A method of calibrating for a near infrared analytical testing device configured to screen for ethanol production yield of an ethanol-producing material, the method comprising:
  grinding an agricultural material to form a sample material;
  collecting a first near infrared signal associated with the sample material with a near infrared testing device, the first near infrared signal being associated with a characteristic parameter of the sample material, the characteristic parameter being capable of enabling evaluation of ethanol production yield for plant material corresponding substantially in composition to the sample material;
  drying the sample material to a substantially standard moisture level;
  collecting a second near infrared signal with the near infrared testing device, the second near infrared signal being associated with the characteristic parameter;
  fermenting the sample material;
  collecting a reference measurement associated with the sample material with a gas chromatography testing device, the reference measurement being associated with the characteristic parameter; and
  correlating the reference measurement to at least one of the first and second near infrared signals so as to build a calibration model used to evaluate ethanol production yield of plant material corresponding substantially in composition to the sample material.

31. A method according to claim 30 wherein grinding an agricultural material comprises grinding an agricultural material comprising one of agricultural seed and stover.

32. A method according to claim 30 wherein grinding an agricultural material comprises grinding an agricultural material to form a sample material comprising one of flour and raw starch material.

* * * * *